(12) United States Patent
Gillies et al.

(10) Patent No.: US 7,169,904 B2
(45) Date of Patent: Jan. 30, 2007

(54) IMMUNOCYTOKINE SEQUENCES AND USES THEREOF

(75) Inventors: Stephen D. Gillies, Carlisle, MA (US); Kin-Ming Lo, Lexington, MA (US); Susan X. Qian, Concord, MA (US)

(73) Assignee: EMD Lexigen Research Center Corp., Billerica, MA (US)

( * ) Notice: Subject to any disclaimer, the term of this patent is extended or adjusted under 35 U.S.C. 154(b) by 0 days.

(21) Appl. No.: 10/737,208

(22) Filed: Dec. 16, 2003

(65) Prior Publication Data

US 2004/0203100 A1     Oct. 14, 2004

Related U.S. Application Data

(60) Provisional application No. 60/433,945, filed on Dec. 17, 2002.

(51) Int. Cl.
    *C07K 16/00*     (2006.01)
(52) U.S. Cl. .................. 530/387.3; 530/387.9; 530/388.1
(58) Field of Classification Search ............. 530/387.1, 530/388.1, 389.1
    See application file for complete search history.

(56) References Cited

U.S. PATENT DOCUMENTS

| | | |
|---|---|---|
| 4,196,265 A | 4/1980 | Koprowski et al. |
| 4,469,797 A | 9/1984 | Albarella |
| 4,522,811 A | 6/1985 | Eppstein et al. |
| 4,667,016 A | 5/1987 | Lai et al. |
| 4,676,980 A | 6/1987 | Segal et al. |
| 4,703,008 A | 10/1987 | Lin |
| 4,732,683 A | 3/1988 | Georgiades et al. |
| 4,737,462 A | 4/1988 | Mark et al. |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,196,320 A * | 3/1993 | Gillies ................. 435/69.7 |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,589,466 A | 12/1996 | Felgner et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |

(Continued)

FOREIGN PATENT DOCUMENTS

AU     21725/88     3/1989

(Continued)

OTHER PUBLICATIONS

Alberts et al., The Cell 2002, Garland Science, 4th edition, esp. p. 161: Figure 3-42.*
Demirci and Li, 2004, Cell Mol. Immunol., 1(2):123-128 (abstract).*
U.S. Appl. No. 07/348,237, May 5, 1989, Rosenblum et al.
Abaza et al., (1992), "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *Journal of Protein Chemistry*, 11(5):433-444.
Abstract XP-002116766, Lupulescu, (1996), "Prostaglandins, Their Inhibitors and Cancer," *Prostaglandins, Leukotrienes and Essential Fatty Acids*, 54(2):83-94.

(Continued)

*Primary Examiner*—Gary B. Nickol
*Assistant Examiner*—Xiaozhen Xie
(74) *Attorney, Agent, or Firm*—Kirkpatrick & Lockhart Nicholson Graham LLP

(57) ABSTRACT

The invention provides a family of antibodies that specifically bind the human cell surface glycosphingolipid GD2. The antibodies comprise modified variable regions, more specially, modified framework regions, which reduce their immunogenicity when administered to a human. The antibodies may be coupled to a therapeutic agent and used in the treatment of cancer.

5 Claims, 11 Drawing Sheets

U.S. PATENT DOCUMENTS

| | | |
|---|---|---|
| 5,728,552 A | 3/1998 | Fujisawa et al. |
| 5,733,876 A | 3/1998 | O'Reilly et al. |
| 5,738,852 A | 4/1998 | Robinson et al. |
| 5,756,349 A | 5/1998 | Lin |
| 5,756,461 A | 5/1998 | Stephens |
| 5,759,551 A | 6/1998 | Ladd et al. |
| 5,770,195 A | 6/1998 | Hudziak et al. |
| 5,795,779 A | 8/1998 | McCormick |
| 5,800,810 A | 9/1998 | Doyle et al. |
| 5,807,715 A | 9/1998 | Morrison et al. |
| 5,827,516 A | 10/1998 | Urban et al. |
| 5,827,703 A | 10/1998 | Debs et al. |
| 5,837,682 A | 11/1998 | Folkman et al. |
| 5,837,821 A | 11/1998 | Wu et al. |
| 5,843,423 A | 12/1998 | Lyman et al. |
| 5,854,205 A | 12/1998 | O'Reilly et al. |
| 5,856,298 A | 1/1999 | Strickland |
| 5,858,347 A | 1/1999 | Bauer et al. |
| 5,885,795 A | 3/1999 | O'Reilly et al. |
| 5,886,178 A | 3/1999 | Allen et al. |
| 5,888,772 A | 3/1999 | Okasinski et al. |
| 5,891,680 A | 4/1999 | Lieschke et al. |
| 5,908,626 A | 6/1999 | Chang et al. |
| 5,922,685 A | 7/1999 | Rakhmilevich et al. |
| 5,955,422 A | 9/1999 | Lin |
| 5,994,104 A | 11/1999 | Anderson et al. |
| 5,994,126 A | 11/1999 | Steinman et al. |
| 6,080,409 A | 6/2000 | Laus et al. |
| 6,086,875 A | 7/2000 | Blumberg et al. |
| 6,100,387 A | 8/2000 | Herrmann et al. |
| 6,169,070 B1 | 1/2001 | Chen et al. |
| 6,171,588 B1 | 1/2001 | Carron et al. |
| 6,231,536 B1 | 5/2001 | Lentz |
| 6,277,375 B1 | 8/2001 | Ward |
| 6,281,010 B1 | 8/2001 | Gao et al. |
| 6,284,536 B1 | 9/2001 | Morrison et al. |
| 6,291,158 B1 | 9/2001 | Winter et al. |
| 6,309,636 B1 * | 10/2001 | do Couto et al. ........ 424/133.1 |
| 6,335,176 B1 | 1/2002 | Inglese et al. |
| 6,340,742 B1 | 1/2002 | Burg et al. |
| 6,348,192 B1 | 2/2002 | Chan et al. |
| 6,406,689 B1 | 6/2002 | Falkenberg et al. |
| 6,429,199 B1 | 8/2002 | Krieg et al. |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,506,405 B1 | 1/2003 | Desai et al. |
| 6,551,592 B2 | 4/2003 | Lindhofer et al. |
| 6,583,272 B1 | 6/2003 | Bailon |
| 6,586,398 B1 | 7/2003 | Kinstler et al. |
| 6,617,135 B1 | 9/2003 | Gillies et al. |
| 6,627,615 B1 | 9/2003 | Debs et al. |
| 6,646,113 B1 | 11/2003 | Dreyfuss et al. |
| 6,777,540 B1 * | 8/2004 | Okumura et al. ........ 530/387.9 |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |

FOREIGN PATENT DOCUMENTS

| | | |
|---|---|---|
| CN | 93100115.3 | 7/1993 |
| DE | 37 12985 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 601 043 B1 | 6/1994 |
| EP | 0 640 619 A1 | 3/1995 |
| EP | 0 668 353 A1 | 8/1995 |
| EP | 0 699 755 A2 | 3/1996 |
| EP | 0 428 596 B1 | 4/1996 |
| EP | 0 706 799 A2 | 4/1996 |
| EP | 0 428 267 B1 | 12/1996 |
| EP | 0 790 309 A1 | 8/1997 |
| EP | 0 433 827 B1 | 3/1998 |
| EP | 0 668 351 B1 | 9/1999 |
| EP | 1 088 888 A1 | 4/2001 |
| GB | 2 188 638 | 10/1987 |
| GB | 2 292 382 A | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08801 | 5/1992 |
| WO | WO 95/08495 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |

| | | |
|---|---|---|
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/52796 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 | 12/2000 |
| WO | WO 01/07081 | 2/2001 |
| WO | WO 01/10912 | 2/2001 |
| WO | WO 01/36489 | 5/2001 |
| WO | WO 01/58957 | 8/2001 |
| WO | WO 02/02143 | 1/2002 |
| WO | WO 02/066514 | 8/2002 |
| WO | WO 02/069232 | 9/2002 |
| WO | WO 02/072605 | 9/2002 |
| WO | WO 02/074783 | 9/2002 |
| WO | WO 02/079232 | 10/2002 |
| WO | WO 02/079415 | 10/2002 |
| WO | WO 02/090566 | 11/2002 |
| WO | WO 03/015697 | 2/2003 |
| WO | WO 03/048334 | 6/2003 |
| WO | WO 03/077834 | 9/2003 |

OTHER PUBLICATIONS

Afonso et al., (1994), "The Adjuvant Effect of Interleukin-12 in a Vaccine Against Leishmania Major," *Science*, 263:235-237.

Angal et al., (1993), "A Single Amino Acid Substitution Abolishes the Heterogeneity of Chimeric Mouse/Human (IgG4) Antibody," *Molecular Immunology*, 30(1):105-108.

Arenberg et al., (1996), "Interferon-γ-inducible Protein 10 (IP-10) is an Angiostatic Factor that Inhibits Human Non-small Cell Lung Cancer (NSCLC) Tumorigenesis and Spontaneous Metastases," *J. Exp. Med.*, 184:981-992.

Bacha et al., (1988), "Interleukin 2 Receptor-Targeted Cytotoxicity: Interleukin 2 Receptor-mediated Action of a Diphtheria Toxin-related Interleukin 2 Fusion Protein," *J. Exp. Med.*, 167:612-622.

Bachelot et al., (1998), "Retrovirus-Mediated Gene Tranfer of an Angiostatin-Endostatin Fusion Protein with Enhanced Anti-Tumor Properties In Vivo," *Proceedings of the Annual Meeting of the American Association for Cancer Research*, 39:271, Abstract #1856 (XP-002089298).

Barnett et al., (1994), "Purification, Characterization and Selective Inhibition of Human Prostaglandin G/H Synthase 1 and 2 Expressed in the Baculovirus System," *Biochimica et Biophysica Acta*, 1209:130-139.

Baselga et al., (1998), "Recombinant Humanized Anti-HER2 Antibody (Herceptin ™) Enhances the Antitumor Activity of Paclitaxel and Doxorubicin against HER3/*neu* Overexpressing Human Breast Cancer Xenogratfs," *Cancer Research*, 58:2825-2831.

Batova et al., (1999), "The Ch14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263.

Batra et al., (1993), "Insertion of Constant Region Domains of Human IgG1 into CD4-PE40 Increases Its Plasma Half-Life," *Molecular Immunology*, 30(4):379-386.

Becker et al., (1996), "An Antibody-Interleukin 2 Fusion Protein Overcomes Tumor Heterogeneity by Induction of a Cellular Immune Response," *Proc. Natl. Acad. Sci. USA*, 93:7826-7831.

Becker et al., (1996), "Eradication of Human Hepatic and Pulmonary Melanoma Metastases in SCID Mice by Antibody-interleukin 2 Fusion Proteins," *Proc. Natl. Acad. Sci. USA*, 93:2702-2707.

Becker et al., (1996), "Long-lived and Transferable Tumor Immunity in Mice after Targeted Interleukin-2 Therapy," *J. Clin. Invest.*, 98(12):2801-2804.

Becker et al., (1996), "T Cell-mediated Eradication of Murine Metastatic Melanoma Induced by Targeted Interleukin-2 Therapy," *J. Exp. Med.*, 183(50):2361-2366.

Beutler et al., (1988), "Tumor Necrosis, Cachexia, Shock, and Inflammation: A Common Mediator," *Annual Rev. Biochem.*, 57:505-518.

Bissery et al., (1997), "The Taxoids," in *Cancer Therapeutics: Experimental and Clinical Agents*, Teicher (ed.), pp. 175-193.

Bitonti et al., (2002), "Transepithelial Absorption of an Erythropoietin-Fc Fusion Protein After Delivery to the Central Airways," *Respiratory Drug Delivery*, 8:309-312.

Bjorn et al., (1985), "Evaluation of Monoclonal Antibodies for the Development of Breast Cancer Immunotoxins," *Cancer Research*, 45:1214-1221.

Boehm et al., (1997), "Antiangiogenic Therapy of Experimental Cancer Does Not Induce Acquired Drug Resistance," *Nature*, 390:404-407.

Boehm et al., (1998), "Zinc-Binding of Endostatin Is Essential for Its Antiangiogenic Activity," *Biochemical and Biophysical Research Communications*, 252:190-194.

Boissel et al., (1993), "Erythropoietin Structure-Function Relationships: Mutant Proteins that Test a Model of Tertiary Structure," *The Journal of Biological Chemistry*, 268(21):15983-15993.

Briggs et al., (1974), "Hepatic Clearance of Intact and Desialylated Erythropoietin," *American Journal of Physiology*, 227(6):1385-1388.

Brooks et al., (1994), "Integrin $\alpha_v\beta_3$ Antagonists Promote Tumor Regression by Inducing Apoptosis of Angiogenic Blood Vessels," *Cell*, 79:1157-1164.

Buchli et al., (1993), "Structural and Biologic Properties of a Human Aspartic Acid-126 Interleukin-2 Analog," *Archives of Biochemistry and Biophysics*, 307(2):411-415.

Burgess et al., (1990), "Possible Dissociation of the Heparin-binding and Mitogenic Activities of Heparin-Binding (Acidic Fibroblast) Growth Factor-1 from Its Receptor-binding Activities by Site-directed Mutagenesis of a Single Lysine Residue," *Journal of Cell Biology*, 111:2129-2138.

Canfield et al., (1991), "The Binding Affinity of Human IgG for its High Affinity Fc Receptor is Determined by Multiple Amino Acids in the CH2 Domain and Is Modulated by the Hinge Region," *J. Exp. Med.*, 173(6):1483-1491.

Cao et al., (1996), "Kringle Domains of Human Angiostatin: Characterization of the Anti-Proliferative Activity of Endothelial Cells," *The Journal of Biological Chemistry*, 271(46):29461-29467.

Cao et al., (1997), "Kringle 5 of Plasminogen is a Novel Inhibitor of Endothelial Cell Growth," *The Journal of Biological Chemistry*, 272(36):22924-22928.

Capon et al., (1989), "Designing CD4 Immunoadhesins for AIDS Therapy," *Nature*, 337:525-531.

Caton et al., (1986), "Structural and Functional Implications of a Restricted Antibody Response to a Defined Antigenic Region on the Influenza Virus Hemagglutinin," *The EMBO Journal*, 5(7):1577-1587.

Chan et al., (1991), "Induction of Interferon γ Production by Natural Killer Cell Stimulatory Factor: Characterization of the Responder Cells and Synergy with Other Inducers," *J. Exp. Med.*, 173: 869-879.

Chang et al., (1989), "Overview of Interleukin-2 as an Immunotherapeutic Agent," *Seminars in Surgical Oncology*, 5:385-390.

Chang et al., (1996), "A Point Mutation in Interleukin-2 that Alters Ligand Internalization," *Journal of Biological Chemistry*, 271(23):13349-13355.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Chaudhary et al., (1988), "Selective Killing of HIV-infected Cells by Recombinant Human CD4-*Pseudomonas* Exotoxin Hybrid Protein," *Nature*, 335:370-372.

Chaudhary et al., (1989), "A Recombinant Immunotoxin Consisting of Two Antibody Variable Domains Fused to *Pseudomonas* Exotoxin," *Nature*, 339:394-397.

Chen et al., (1997),"Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodiner," *Journal of Immunology*, 159(1):351-358.

Cheon et al., (1994), "High-affinity Binding Sites for Related Fibroblast Growth Factor Ligands Reside Within Different Receptor Immunoglobulin-like Domains," *Proc. Natl. Acad. Sci. USA*, 91: 989-993.

Chuang et al., (1993), "Effect of New Investigational Drug Taxol on Oncolytic Activity and Stimulation of Human Lymphocytes," *Gynecologic Oncology*, 49:291-298.

Chuang et al., (1994), "Alteration of Lymphocyte Microtubule Assembly, Cytotoxicity, and Activation by the Anticancer Drug Taxol," *Cancer Research*, 54:1286-1291.

Cohen et al., (1996), "Human Leptin Characterization," *Nature*, 382:589.

Cole et al., (1997), "Human IgG2 Variants of Chimeric Anti-CD3 Are Nonmitogenic to T Cells," *Journal of Immunology*, 159:3613-3621.

Collins et al., (1988), "Identification of Specific Residues of Human Interleukin 2 That Affect Binding to the 70-kDa Subunit (p70) of the Interleukin 2 Receptor," *Proc. Natl. Acad. Sci. USA*, 85:7709-7713.

Colombo et al., (1996), "Amount of Interleukin 12 Available at the Tumor Site is Critical for Tumor Regression," *Cancer Research*, 56:2531-2534.

Conner et al., (2004), "Ex vivo Evaluation of Anti-EpCAM Immunocytokine huKS-IL2 in Ovarian Cancer," *J. Immunotherapy*, 27:211-219.

Cruse et al., (eds.), (1995), *Illustrated Dictionary of Immunology*, pp. 156-158, CRC Press, NY.

D'Amato et al., (1994), "Thalidomide is an Inhibitor of Angiogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anticancer Immunity," *Cancer Immunol. Immunother.*, 52:297-308.

de la Salle et al., (1996), "FcγR on Human Dendritic Cells," in *Human IgG Receptors*, pp. 39-55, van de Winkel et al. (eds.), R.G. Landes Co.

Ding et al., (1988), "Zinc-Dependent Dimers Observed in Crystals of Human Endostatin," *Proc. Natl. Acad. Sci. USA*, 95:10443-10448.

Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.

Dorai et al., (1991), "Agylcosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Duncan et al., (1988), "The Binding Site for Clq on IgG," *Nature*, 332:738-740.

Earnest et al., (1992), "Piroxicam and Other Cyclooxygenase Inhibitors: Potential for Cancer Chemoprevention," *J. Cell. Biochem., Supp.*, 161:156-166.

Egrie et al., (2001), "Development and Characterization of Novel Erythropoiesis Stimulating Protein (NESP)," *Nephrol. Dial. Transplant.*, 16(Supp 3):3-13.

Eisenthal, (1990), "Indomethacin Up-regulates the Generation of Lymphokine-Activated Killer-cell Activity and Antibody-dependent Cellular Cytotoxicity Mediated by Interleukin-2," *Cancer Immunol. Immunother.*, 31:342-348.

Elliott et al., (1996), "Fine-Structure Epitope Mapping of Antierythropoietin Monoclonal Antibodies Reveals a Model of Recombinant Human Erythropoietin Structure," *Blood*, 87(7):2702-2713.

Elliott et al., (1997), "Mapping of the Active Site of Recombinant Human Erythropoietin," *Blood*, 89(2):493-502.

Fell et al., (1991), "Genetic Construction and Characterization of A Fusion Protein Consisting of a Chimeric F(ab') with Specificity for Carcinomas and Human IL-2," *J. Immunology*, 146(7):2446-2452.

Fell et al., (1992), "Chimeric L6 Anti-tumor Antibody: Genomic Construction, Expression, and Characterization of the Antigen Binding Site," *J. Biological Chemistry*, 267:15552-15558.

Fibi et al., (1995), "N- and O-Glycosylation Muteins of Recombinant Human Erythropoietin Secreted From BHK-21 Cells," *Blood*, 85(5):1229-1236.

Friedman et al., (1998), "Leptin and the Regulation of Body Weight in Mammals," *Nature*, 395:763-770.

Frost et al., (1997), "A Phase 1/1B Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific Enzyme-linked Immunosorbent Assays for Quantitation of Antibody-cytokine Fusion Proteins," *Clinical and Diagnostic Laboratory Immunology*, 6(2):236-42.

Gasson et al., (1984), "Purified Human Granulocyte Colony-Stimulating Factor: Direct Action on Neutrophils," *Science*, 226:1339-1342.

Gately et al., (1998), "The Interleukin-12/Interleukin-12-Receptor System: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist," *Eur. J. Immunol.*, 25:200-206.

Gillies et al., (1989), "Expression of Human Anti-Tetanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen Binding and Biological Activities of Engineered Mutant Chimeric Antibodies with Human Tumor Specificities," *Hum. Antibod. Hybridomas*, 1(1):47-54.

Gillies et al., (1991), "Expression of Genetically Engineered Immunoconjugates of Lymphotoxin and a Chimeric Antiganglioside GD2 Antibody," *Hybridoma.*, 10(3):347-56.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/ Recombinant Antibody," *J. Immunology*, 146(3):1067-1071.

Gillies et al., (1992), "Antibody-Targeted Interleukin 2 Stimulates T-Cell Killing of Autologous Tumor Cells," *Proc. Natl. Acad. Sci. USA*, 89:1428-1432.

Gillies et al., (1993), "Biological Activity and *In Vivo* Clearance of Antitumor Antibody/Cytokine Fusion Proteins," *Bioconjugate Chem.*, 4(3):230-235.

Gillies et al., (1998), "Antibody-IL-12 Fusion Proteins are Effective in SCID Mouse Models of Prostate and Colon Carcinoma Metastases," *J. Immunology*, 160:6195-6203.

Gillies et al., (1999), "Improving the Efficacy of Antibody-Interleukin 2 Fusion Proteins by Reducing Their Interaction with Fc Receptors," *Cancer Research*, 59:2159-2166.

Gillies et al., (2002), "Bi-functional Cytokine Fusion Proteins for Gene Therapy and Antibody-targeted Treatment of Cancer," *Cancer Immunol. Immunother.*, 51(8):449-60.

Gillies et al., (2002), "Improved Circulating Half-life and Efficacy of an Antibody-interleukin 2 Immunocytokine Based on Reduced Intracellular Proteolysis," *Clin. Cancer Research*, 8(1):210-216.

Gillis et al., (1978), "T Cell Growth Factor: Parameters of Production And A Quantitative Microassay for Activity," *J. Immunology*, 120(6):2027-2032.

Goeddel et al., (1986), "Tumor Necrosis Factors: Gene Stucture and Biological Activities," *Cold Spring Harb. Symp. Quant. Biol.*, 51:597-609.

Greene et al., (1975), "Neuronal Properties of Hybrid Neuroblastoma X Sympathetic Ganglion Cells," *Proc. Natl. Acad. Sci. USA*, 72(12):4923-4927.

Gren et al., (1983), "A New Type of Leukocytic Interferon," English Translation of *Dokl. Akad. Nauk. SSSR.*, 269(4):986-990.

Griffon-Etienne et al., (1999), "Taxane-induced Apoptosis Decompresses Blood Vessels and Lowers Interstitial Fluid Pressure in Solid Tumors: Clinical Implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.

Guyre et al., (1997), "Increased Potency of Fc-receptor-targeted Antigens," *Cancer Immunol. Immunother.*, 45:146-148.

Hammerling et al., (1996), "In Vitro Bioassay for Human Erythropoietin Based on Proliferative Stimulation of an Erythroid Cell Line and Analysis of Carbohydrate-dependent Microheterogeneity," *Journal of Pharmaceutical and Biomedical Analysis*, 14:1455-1469.

Handgretinger et al., (1995), "A Phase I Study of Human/Mouse Chimeric Anti-ganglioside GD2 Antibody ch14.18 in Patients with Neuroblastoma," *European J. Cancer*, 31A(2):261-267.

Hank et al., (1996), "Activation of Human Effector Cells by a Tumor Reactive Recombinant Anti-ganglioside GD2 Interleukin-2 Fusion Protein (ch14.18-IL2)," *Clin Cancer Research*, 2(12):1951-1959.

Hank et al., (2003), "Determination of Peak Serum Levels and Immune Response to the Humanized Anti-ganglioside Antibody-interleukin-2 Immunocytokine," in *Methods in Molecular Medicine, vol. 85: Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,8-sialyltransferase cDNA using anti-GD2 Monoclonal Antibody," *Proc. Natl. Acad. Sci. USA*, 91(22):10455-10459.

Harris et al., (1993), "Therapeutic Antibodies—the Coming of Age," *Trends in Biotechnology*, 11:42-44.

Harris, (1995), "Processing of C-terminal Lysine and Arginine Residues of Proteins Isolated from Mammalian Cell Culture," *J. Chromatography A*, 705:129-134.

Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.

Harvill et al., (1996), "In Vivo Properties of an IgG3-IL-2 Fusion Protein: A General Strategy for Immune Potentiation," *J. Immunology*, 157(7):3165-3170.

Hazama et al., (1993), "Adjuvant-Independent Enhanced Immune Responses to Recombinant Herpes Simplex Virus Type 1 Glycoprotein D by Fusion with Biologically Active Interleukin-2," *Vaccine*, 11(6):629-636.

He et al., (1998), "Humanization and Pharmacokinetics of a Monoclonal Antibody with Specificity for Both E- and P-Selectin," *J. Immunology*, 160:1029-1035.

Heijnen et al., (1996), "Antigen Targeting to Myeloid-specific Human FcγRI/CD64 Triggers Enhanced Antibody Responses in Transgenic Mice," *J. Clin. Invest.*, 97(2):331-338.

Heinzel et al., (1997), "In Vivo Production and Function of IL-12 p40 Homodimers," *J. Immunology*, 158:4381-4388.

Hellstrom et al., (1986), "Antitumor Effects of L6, an IgG2a Antibody that Reacts with Most Human Carcinomas," *Proc. Natl. Acad. Sci. USA*, 83: 7059-7063.

Henkart, (1985), "Mechanism of Lymphocyte-Mediated Cytotoxicity," *Ann. Rev. Immunol.*, 3:31-58.

Herrmann et al., (1989), "Hematopoietic Responses With Advanced Malignancy Treated With Recombinant Human Granulocyte-Macrophage Colony-Stimulating Factor," *Journal of Clinical Oncology*, 7(2):159-167.

Hezareh et al., (2001), "Effector Function Activities of a Panel of Mutants of a Broadly Neutralizing Antibody against Human Immunodeficiency Virus Type 1," *J. Virology*, 75(24):12161-12168.

Hohenester et al., (1998), "Crystal Structure of the Angiogenesis Inhibitor Endostatin at 1.5 Å Resolution," *EMBO Journal*, 17(6):1656-1664.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).

Holden et al., (2001), "Augmentation of Antitumor Activity of an Antibody-Interleukin 2 Immunocytokine with Chemotherapeutic Agents," *Clinical Cancer Research*, 7:2862-2869.

Hoogenboom et al., (1991), "Construction and Expression of Antibody-tumor Necrosis Factor Fusion Proteins," *Molecular Immunology*, 28(9):1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096(4):345-354 (Abstract).

Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.

Hu et al., (1996), "A Chimeric Lym-1/Interleukin 2 Fusion for Increasing Tumor Vascular Permeability and Enhancing Antibody Uptake," *Cancer Research*, 56:4998-5004.

Huck et al., (1986), "Sequence of a Human Immunoglobulin Gamma 3 Heavy Chain Constant Region Gene: Comparison With the Other Human Cγ genes," *Nucleic Acids Research*, 14(4):1779-1789.

Hurn et al., (1980), "Production of Reagent Antibodies," *Methods in Enzymology*, 70: 104-142.

Huse et al., (1989), "Generation of a Large Combinatorial Library of the Immunoglobulin Repertoire in Phage Lambda," *Science*, 246:1275-1281.

Idusogie et al., (2000), "Mapping of the Clq Binding Site on Rituxan, a Chimeric Antibody with a Human IgG1 Fc," *J. Immunology*, 164(8):4178-4184.

Imboden et al., (2001), "The Level of MHC Class 1 Expression on Murine Adenocarcinoma Can Change the Antitumor Effector Mechanism of Immunocytokine Therapy," *Cancer Research*, 61(4):1500-7.

Ingber et al., (1990), "Synthetic Analogues of Fumagillin that Inhibit Angiogenesis and Suppress Tumour Growth," *Nature*, 348:555-557.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Jones et al., (1986), "Replacing the Complementarity-determining Regions in a Human Antibody with Those from a Mouse," *Nature*, 321:522-525.

Ju et al., (1987), "Structure-Function Analysis of Human Interleukin-2: Identification of Amino Acid Residues for Biological Activity," *Journal of Biological Chemistry*, 262(12):5723-5731.

Jung et al., (1986), "Activation of Human Peripheral Blood Mononuclear Cells by Anti-T3: Killing of Tumor Target Cells Coated with Anti-target-anti-T3 Conjugates," *Proc. Natl. Acad. Sci. USA*, 83:4479-4483.

Junghans et al., (1996), "The Protection Receptor IgG Catabolism is the B2-microglobulin-containing Neonatal Intestinal Transport Receptor," *Proc. Natl. Acad. Sci. USA*, 93(11):5512-5516.

Kang et al., (1991), "Antibody Redesign by Chain Shuffling from Random Combinatorial Immunoglobulin Libraries," *Proc. Natl. Acad. Sci. USA*, 88:11120-11123.

Kappel et al., (1992), "Regulating Gene Expression in Transgenic Animals," *Current Opinion in Biotechnology*, 3:548-553.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26(2):126-131.

Karpovsky et al., (1984), "Production of Target-Specific Effector Cells using Hetero-Cross Linked Aggregate Containing Anti-Target Cell and AntiFcγ Receptor Antibodies," *Journal of Experimental Medicine*, 1609(6):1686-1701.

Kendra et al., (1999),"Pharmacokinetics and Stability of the ch14.18-Interleukin-2 Fusion Protein in Mice," *Cancer Immunol. Immunother.*, 48:219-229.

Kim et al., (1997),"An Ovalbumin-IL-12 Fusion Protein is More Effective than Ovalbumin Plus Free Recombinant IL-12 in Inducing a T Helper Cell Type 1-dominated Immune Response and Inhibiting Antigen-Specific IgE Production," *J. Immunology*, 158(9):4137-4144.

Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.

Kitamura et al., (1989), "Establishment and Characterization of a Unique Human Cell Line that Proliferates Dependently on GM-CSF, IL-3, or Erythropoietin," *Journal of Cellular Physiology*, 140:323-334.

Ko et al., (2004), "Safety, Pharmacokinetics, and Biological Pharmacodynamics of the Immunocytokine EMD 273066 (huKS-IL2)," *J. Immunotherapy*, 27:232-239.

Kranz et al., (1984), "Attachment of an Anti-receptor Antibody to Non-target Cells Renders Them Susceptible to Lysis by a Clone of Cytotoxic T Lymphocytes," *Proc. Natl. Acad. Sci. USA*, 81:7922-7926.

Kuo et al., (2001), "Oligomerization-dependent Regulation of Motility and Morphogenesis by the Collagen XVIII NC1/Endostatin Domain," *Journal of Cell Biology*, 152(6):1233-1246.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

LaVallie et al., (1993), "Cloning and Functional Expression of a cDNA Encoding the Catalytic Subunit of Bovine Enterokinase," *Journal of Biological Chemistry*, 268(31):23311-23317.

Lazar et al., (1988), "Transforming Growth Factor α: Mutation of Aspartic Acid 47 and Leucine 48 Results in Different Biological Activities," *Molecular and Cellular Biology*, 8(3):1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lieschke, et al., (1997), "Bioactive Murine and Human Interleukin-12 Fusion Proteins which Retain Antitumor Activity In Vivo," *Nature Biotechnology*, 15(1):35-40.

Linsley et al., (1991), "CTLA-4 is a Second Receptor for B Cell Activation B7," *J. Exp. Med.*, 174(3):561-569.

Liu et al., (1985), "Heteroantibody Duplexes Target Cells for Lysis by Cytotoxic T Lymphocytes," *Proc. Natl. Acad. Sci. USA*, 82:8648-8652.

Liu et al., (1988), "Hormone Conjugated with Antibody to CD3 Mediates Cytotoxic T Cell Lysis of Human Melanoma Cells," *Science*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92(10):3730-3736.

Lo et al., (1992), "Expression and Secretion of an Assembled Tetrameric CH2-deleted Antibody in *E. coli,* " *Hum. Antibod. Hybridomas*, 3:123-128.

Lo et al., (1998), "High Level Expression and Secretion of Fc-X Fusion Proteins in Mammalian Cells," *Protein Engineering*, 11(6):495-500.

Locatelli et al., (2001), "Darbepoetin alfa Amgen," *Current Opinion in Investigational Drugs*, 2:1097-1104.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (1998), "Immunocytokines: A Promising Approach to Cancer Immunotherapy," *Pharmacol. Ther.*, 80(3):277-292.

Lode et al., (1998), "Natural Killer Cell-Mediated Eradication of Neuroblastoma Metastases to Bone Marrow by Targeted Interleukin-2 Therapy," *Blood*, 91(5):1706-1715.

Lode et al., (1999), "Synergy Between an Antiangiogenic Integrin αv Antagonist and an Antibody-cytokine Fusion Protein Eradicates Spontaneous Tumor Metastases," *Proc. Natl. Acad. Sci. USA*, 96:1591-1596.

Lode et al., (1999), "Tumor-targeted IL-2 Amplifies T Cell-mediated Immune Response Induced by Gene Therapy with Single-chain Il-12," *Proc. Natl. Acad. Sci. USA*, 96:8591-8596.

Lode et al., (2000), "Amplification of T Cell Mediated Immune Responses by Antibody-Cytokine Fusion Proteins," *Immunological Investigations*, 29(2):117-120.

Lode et al., (2000), "What To Do With Targeted IL-2," *Drugs of Today*, 36(5):321-336.

Lode et al., (2000), "Melanoma Immunotherapy for Targeted IL-2 Depends on CD4(+) T-cell Help Mediated by CD40/CD40L Interaction," *J. Clin. Invest.*, 105(11):1623-30.

Macdougall, (2002), "Optimizing the Use of Erythropoietic Agents—Pharmacokinetics and Pharmacodynamic Considerations," *Nephrol. Dial. Transplant.*, 17 (Supp 5):66-70.

Maecker et al., (1997), "DNA Vaccination with Cytokine Fusion Constructs Biases the Immune Response to Ovalbumin," *Vaccine*, 15(15):1687-1696.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84(8):2457-2466.

Mark et al., (1992), "Expression and Characterization of Hepatocyte Growth Factor Receptor-IgG Fusion Proteins," *Journal of Biological Chemistry*, 267(36):26166-26171.

Martinotti et al., (1995), "CD4 T Cells Inhibit *In Vivo* the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse IgG1," *J. Immunology*, 158(5):2211-2217.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.

Mestre et al., (1997), "Retinoids Suppress Epidermal Growth Factor-induced Transcription of Cyclooxygenase-2 in Human Oral Squamous Carcinoma Cells," *Cancer Research*, 57:2890-2895.

Mosmann et al., (1989), "TH1 and TH2 Cells: Different Patterns of Lymphokine Secretion Lead to Different Functional Properties," *Ann. Rev. Immunol.*, 7:145-173.

Mott et al., (1995), "The Solution Structure of the F42A Mutant of Human Interleukin 2," *J. Mol. Biol.*, 247:979-994.

Mueller et al., (1990), "Enhancement of Antibody-Dependent Cytotoxicity With A Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Mueller et al., (1997), "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Mullins et al., (1997), "Taxol-mediated Changes in Fibrosarcoma-induced Immune Cell Function: Modulation of Antitumor Activities," *Cancer Immunol. Immunother.* 45:20-28.

Mullins et al., (1998), "Interleukin-12 Overcomes Paclitaxel-mediated Suppression of T-cell Proliferation," *Immunopharmacol. Immunotoxicol.*, 20(4):473-492.

Murphy et al., (1986), "Genetic Construction, Expression, and Melanoma-selective Cytotoxicity of a Diphtheria Toxin-related α-melanocyte-stimulating Hormone Fusion Protein," *Proc. Natl. Acad. Sci. USA*, 83:8258-8262.

Murphy, (1988), "Diphtheria-related Peptide Hormone Gene Fusions: A Molecular Gene Approach to Chimeric Toxin Development," in *Immunotoxins*, pp. 123-140, Frankel (ed.), Kluwer Acad. Pub.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Neal et al., (2003), "NXS2 Murine Neuroblastomas Express Increased Levels of MHC Class I Antigens upon Recurrence Following NK-dependent Immunotherapy," *Cancer Immunol. Immunother.*, 53:41-52.

Nedwin et al., (1985), "Human Lymphotoxin and Tumor Necrosis Factor Genes: Structure, Homology and Chromosomal Localization," *Nucleic Acids Research*, 13(17):6361-6373.

Netti et al., (1995), "Time-dependent Behavior of Interstitial Fluid Pressure in Solid Tumors: Implications for Drug Delivery," *Cancer Research*, 55:5451-5458.

Netti et al., (1999), "Enhancement of Fluid Filtration Across Tumor Vessels: Implication for Delivery of Macromolecules," *Proc. Nat. Acad. Sci.USA*, 96:3137-3142.

Neuberger et al., (1984), "Recombinant Antibodies Possessing Novel Effector Functions," *Nature*, 312:604-608.

Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2002) "An Oral DNA Vaccine Against Human Carcinoembryonic Antigen (CEA) Prevents Growth and Dissemination of Lewis Lung Carcinoma in CEA Transgenic Mice," *Vaccine*, 20:421-429.

Niethammer et al., (2001), "Targeted Interleukin 2 Therapy Enhances Protective Immunity Induced by an Autologous Oral DNA Vaccine Against Murine Melanoma," *Cancer Research*, 61(16):6178-84.

Nimtz et al., (1993), "Structures of Sialylated Oligosaccharides of Human Erythropoietin Expressed in Recombinant BHK-21 Cells," *Eur. J. Biochem.*, 213:39-56.

O'Reilly et al., (1994), "Angiostatin: A Novel Angiogenesis Inhibitor That Mediates the Suppression of Metastases by a Lewis Lung Carcinoma," *Cell*, 79:315-328.

O'Reilly et al., (1996), "Angiostatin Induces and Sustains Dormancy of Human Primary Tumors in Mice," *Nature Medicine*, 2(6):689-692.

O'Reilly et al., (1997), "Endostatin: An Endogenous Inhibitor of Angiogenesis and Tumor Growth," *Cell*, 88:277-285.

Pancook et al., (1996), "Eradication of Established Hepatic Human Neuroblastoma Metastases in Mice with Severe Combined Immunodeficiency by Antibody-targeted Interleukin-2," *Cancer Immunol. Immunother.*, 42(2):88-92.

Park et al., (2000), "Efficiency of Promoter and Cell Line in High-level Expression of Erythropoietin," *Biotechnol. Appl. Biochem.*, 32:167-172.

Pastan et al., (1989), "*Pseudomonas* Exotoxin: Chimeric Toxins," *Journal of Biological Chemistry*, 264(26):15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target Cell Antibodies," *J. Exp. Med.*, 163:166-178.

Perez et al., (1989), "Isolation and Characterization of a cDNA Encoding the KS1/4 Epithelial Carcinoma Marker," *J. Immunology*, 142(10):3662-3667.

Pertl et al., (2003), "Immunotherapy with a Posttranscriptionally Modified DNA Vaccine Induces Complete Protection Against Metastatic Neuroblastoma," *Blood*, 101(2):649-654.

Polizzi et al., (1999), "A Novel Taxane with Improved Tolerability and Therapeutic Activity in a Panel of Human Tumor Xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Natl. Acad. Sci. USA*, 94(20):10889-10894.

Reisfeld et al., (1994), "Potential of Genetically Engineered Anti-Ganglioside GD2 Antibodies for Cancer Immunotherapy," *Prog. Brain Res.*, 101:201-212.

Reisfeld et al., (1996), "Antibody-interleukin 2 Fusion Proteins: A New Approach to Cancer Therapy," *J. Clin. Lab. Anal.*, 10:160-166.

Reisfeld et al., (1996), "Involvement of B Lymphocytes in the Growth Inhibition of Human Pulmonary Melanoma Metastases in Athymic *nu/nu* Mice by an Antibody-lymphotoxin Fusion Protein," *Cancer Research*, 56(8):1707-1712.

Reisfeld et al., (1996), "Recombinant Antibody Fusion Proteins for Cancer Immunotherapy," *Current Topics in Microbiology and Immunology*, 213:27-53.

Reisfeld et al., (1997), "Immunocytokines: A New Approach to Immunotherapy of Melanoma," *Melanoma Research*, 7(Supp2):S99-S106.

Riethmuller et al., (1994), "Randomised Trial of Monoclonal Antibody for Adjuvant Therapy of Resected Dukes' C Colorectal Carcinoma," *The Lancet*, 343:1177-1183.

Roessler et al., (1994), "Cooperative Interactions Between the Interleukin 2 Receptor α and β Chains Alter the Interleukin 2-binding Affinity of the Receptor Subunits," *Proc. Natl. Acad. Sci. USA*, 91:3344-3347.

Roitt et al., (1993), "The Role of TH Cells in the Selection of Effector Mechanisms Directed Against Target Antigens," *Immunology*, 3rd Ed., pp. 8.3-8.4.

Rosenberg, (1988), "Immunotherapy of Cancer Using Interleukin 2: Current Status and Future Prospects," *Immunology Today*, 9(2):58-62.

Rozwarski et al., (1994), "Structural Comparisons Among the Short-chain Helical Cytokines," *Structure*, 2(3):159-173.

Ruehlmann et al., (2001), "MIG (CIXCL9) Chemokine Gene Therapy Combines with Antibody-cytokine Fusion Protein to Suppress Growth and Dissemination of Murine Colon Carcinoma," *Cancer Research*, 61(23):8498-503.

Sabzevari et al., (1994), "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.

Saleh et al., (1992), "Phase 1 Trial of the Chimeric Anti-GD2 Monoclonal Antibody ch14.18 in Patients With Malignant Melanoma," *Hum. Antiob. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, 179:1109-1118.

Santon et al., (1986), "Effects of Epidermal Growth Factor Receptor Concentration on Tumorigenicity of A431 Cells in Nude Mice," *Cancer Research*, 46:4701-4705.

Sasaki et al., (1998), "Structure, Function and Tissue Forms of the C-terminal Globular Domain of Collagen XVIII Containing the Angiogenesis Inhibitor Endostatin," *EMBO Journal*, 17(15):4249-4256.

Sauve et al., (1991), "Localization in Human Interleukin 2 of the Binding Site to the α-chain (p55) of the Interleukin 2 Receptor," *Proc. Natl. Acad. Sci. USA*, 88:4636-4640.

Schlom (1991), "Monoclonal Antibodies: They're More and Less Than You Think," in *Molecular Foundations of Oncology*, pp. 95-133.

Schnee et al., (1987), "Construction and Expression of a Recombinant Antibody-targeted Plasminogen Activator," *Proc. Natl. Acad. Sci. USA*, 84:6904-6908.

Schoenhaut et al., (1992), "Cloning and Expression of Murine IL-12," *J. Immunology*, 148(11):3433-3340.

Seidenfeld et al., (2001), "Epoietin Treatment of Anemia Associated with Cancer Therapy: A Systematic Review and Meta-analysis of Controlled Clinical Trials," *Journal of National Cancer Institute*, 93(16):1204-1214.

Senter et al., (1988), "Anti-tumor Effects of Antibody-alkaline Phosphatase Conjugates in Combination with Etoposide Phosphate," *Proc. Natl. Acad. Sci. USA*, 85(13):4842-4846.

Shanafelt et al., (2000), "A T-cell-Selective Interleukin 2 Mutein Exhibits Potent Antitumor Activity and is Well Tolerated In Vivo," *Nature Biotechnology*, 18:1197-1202.

Sharma et al., (1999), "T cell-derived IL-10 Promotes Lung Cancer Growth by Suppressing Both T cell and APC Function," *Journal of Immunology*, 163:5020-5028.

Shen et al., (1986), "Heteroantibody-Mediated Cytotoxicity: Antibody to the High Affinity Fc Receptor for IgG Mediates Cytotoxicity by Human Monocytes That is Enhanced by Interferon-γ and is Not Blocked by Human IgG," *J. Immunology*,137(11):3378-3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et al., (1990), "Expression and Characterization of an Antibody Binding Specificity Joined to Insulin-like Growth Factor 1: Potential Applications for Cellular Targeting," *Proc. Natl. Acad. Sci. USA*, 87:5322-5326.

Shinkawa et al., (2003), "The Absence of Fucose But Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-3473.

Sim et al., (1997), "A Recombinant Human Angiostatin Protein Inhibits Experimental Primary and Metastatic Cancer," *Cancer Research*, 57:1329-1334.

Spiekermann et al., (2002), "Receptor-mediated Immunoglobulin G Transport Across Mucosal Barriers in Adult-Life: Functional Expression of FcRn in the Mammalian Lung," *J. Exp. Med.*, 196:303-310.

Stevenson et al., (1997), "Conjugation of Human Fcγ in Closed-Hinge or Open-Hinge Configuration to Fab'γ and Analogous Ligands," *J. Immunology*, 158:2242-2250.

Strom et al., (1996), "Therapeutic Approach to Organ Transplantation," Chapter 36, pp. 451-456, in *Therapeutic Immunology*, Austen et al., (eds.), Blackwell Science.

Sulitzeanu, (1993), "Immunosuppressive Factors in Human Cancer," pp. 247-266 in *Advances in Cancer Research*, vol. 60, Vande Woude et al. (eds.), Academic Press, Inc.

Syed et al., (1998), "Efficiency of Signaling Through Cytokine Receptors Depends Critically on Receptor Orientation," *Nature*, 395:511-516.

Taniguchi et al., (1983), "Structure and Expression of a Cloned cDNA for Human Interleukin-2," *Nature*, 302:305-309.

Tao et al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.

Tao et al., (1993), "Structural Features of Human Immunoglobulin G that Determine Isotype-Differences in Complement Activation," *J. Exp. Med.*, 178(2):661-667.

Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 17th Ed., (1999) pp. 990-993 and 1278-1283.

Thommesen et al., (2000), "Lysine 322 in the Human IgG3 Ch2 Domain is Crucial for Antibody Dependent Complement Activation," *Mol. Immunol.*, 37(16):995-1004.

Till et al., (1988), "An Assay that Predicts the Ability of Monoclonal Antibodies to Form Potent Ricin A Chain-containing Immunotoxins," *Cancer Research*, 48(5):1119-1123.

Till et al., (1988), "HIV-Infected Cells are Killed by rCD4-Ricin A Chain," *Science*, 242:1166-1168.

Trinchieri, (1994), "Interleukin-12: A Cytokine Produced by Antigen-Presenting Cells With Immunoregulatory Functions in the Generation of T-Helper Cells Type 1 and Cytotoxic Lymphocytes," *Blood*, 84:4008-4027.

Vagliani et al., (1996), "Interleukin 12 Potentiates that Curative Effect of a Vaccine Based on Interleukin 2-transduced Tumor Cells," *Cancer Research*, 56:467-470.

Varki et al., (1984), "Antigens Associated with a Human Lung Adenocarcinoma Defined by Monoclonal Antibodies," *Cancer Research*, 44:681-687.

Verhoeyen et al., (1988), "Reshaping Human Antibodies: Grafting an Antilysozyme Activity," *Science*, 239:1534-1536.

Villunger et al., (1997), "Constitutive Expression of Fas (Apo-1/CD95) Ligand on Multiple Myeloma Cells: A Potential Mechanism of Tumor-induced Suppression of Immune Surveillance," *Blood*, 90(1):12-20.

Watanabe et al., (1997), "Long-term Depletion of Naive T cells in Patients Treated for Hodgkin's Disease," *Blood*, 90(9):3662-3672.

Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Wells, (1990), "Additivity of Mutational Effect in Proteins," *Biochemistry*, 29(37):8509-8517.

Wen et al., (1993), "Erythropoietin Structure-Function Relationships: High Degree of Sequence Homology Among Mammals," *Blood*, 82(5):1507-1516.

Wen et al., (1994), "Erythropoietin Structure-Function Relationships: Identification of Functionally Important Domains," *J. Biological Chemistry*, 269(36):22839-22846.

Williams et al., (1986), "Production of Antibody-tagged Enzymes by Myeloma Cells: Application to DNA Polymerase I Klenow Fragment," *Gene*, 43:319-324.

Williams et al., (1987), "Diphtheria Toxin Receptor Binding Domain Substitution with Interleukin-2: Genetic Construction and Properties of a Diptheria Toxin-related Interleukin-2 Fusion Protein," *Protein Engineering*, 1(6):493-498.

Wooley et al., (1993), "Influence of a Recombinant Human Soluble Tumor Necrosis Factor Receptor Fc Fusion Protein on Type II Collagen-Induced Arthritis in Mice," *J. Immunology*, 151:6602-6607.

Wu et al., (1997), "Suppression of Tumor Growth with Recombinant Murine Angiostatin," *Biochemical and Biophysical Research Communications*, 236:651-654.

Xiang et al., (1997), "Elimination of Established Murine Colon Carcinoma Metastases by Antibody-Interleukin 2 Fusion Protein Therapy," *Cancer Research*, 57:4948-4955.

Xiang et al., (1998), "Induction of Persistant Tumor-protective Immunity in Mice Cured of Established Colon Carcinoma Metastases," *Cancer Research*, 58(17):3918-3925.

Xiang et al., (1999) "T Cell Memory against Colon Carcinoma is Long-lived in the Absence of Antigen," *J. Immunology*, 163(7):3676-83.

Xiang et al., (2001), "A Dual Function DNA Vaccine Encoding Carcinoembryonic Antigen and CD40 Ligand Trimer Induces T Cell-mediated Protective Immunity Against Colon Cancer Carcinoembryonic Antigen-Transgenic Mice," *J. Immunology*, 167(8):4560-5.

Xiang et al., (2001), "Protective Immunity Against Human Carcinoembryonic Antigen (CEA) Induced by an Oral DNA Vaccine in CEA-transgenic Mice," *Clinical Cancer Research*, 7(3 Supp):S856-S864.

Xu et al., (1994), "Residue at Position 331 in the IgG1 and IgG4 CH2 Domains Contributes to Their Differential Ability to Bind and Activate Complement," *J. Biol. Chem.*, 269(5):3469-3474.

Yu et al., (1998), "Phase I Trial of a Human-Mouse Chimeric Anti-Disaloganglioside Monoclonal Antibody ch14.18 in Patients with Refractory Neuroblastoma and Osteosarcoma," *J. Clinical Oncology*, 16(6):2169-80.

Zagozdzon et al., (1999), "Potentiation of Antitumor Effects of IL-12 in Combination with Paclitaxel in Murine Melanoma Model In Vivo," *International Journal of Molecular Medicine*, 4:645-648.

Zheng et al., (1995), "Administration of Noncytolytic IL-10/Fc in Murine Models of Lipopolysaccharide-induced Septic Shock and Allogenic Islet Transplantation," *J. Immunology*, 154:5590-5600.

Aichele et al., (1994), "Peptide-Induced T-Cell Tolerance to Prevent Autoimmune Diabetes in a Transgenic Mouse Model," *Proc. Natl. Acad. Sci. USA*, 91:444-448.

Altschul et al., (1990), "Basic Local Alignment Search Tool," *J. Mol. Biol.*, 215:403-10.

Altschul et al., (1997), "Gapped BLAST and PSI-BLAST: A New Generation of Protein Database Search Programs," *Nucleic Acids Res.*, 25(17):3389-3402.

Anderson et al., (1980), "Characterization of the Fc Receptor for IgG on a Human Macrophage Cell Line U937," *J. Immunol.*, 125(6):2735-41.

Anderson et al., (1994), "Effects of Route and Formulation on Clinical Pharmacokinetics of Interleukin-2," *Clin. Pharmacokinet.*, 27(1):19-31.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Barbulescu et al., (1998), "IL-12 and IL-18 Differentially Regulate the Transcriptional Activity of the Human IFN-γ Promoter in Primary CD4+ T Lymphocytes," *J. Immunol.*, 160:3642-7.

Bednarek et al., (1991), "Soluble HLA-A2.1 Restricted Peptides that are Recognized by Influenza Virus Specific Cytotoxic T Lymphocytes," *J. Immunol. Methods*, 139:41-47.

Benacerraf et al., (1959), "The Clearance of Antigen Antibody Complexes from the Blood by the Reticulo-Endothelial System," *J. Immunol.*, 82:131-7.

Böhm, (1994), "On the Use of LUDI to Search the Fine Chemicals Directory for Ligands of Proteins of Known Three-Dimensional Structure," *J. Comput. Aided Mol. Des.*, 8:623-32.

Böhm, (1994), "The Development of a Simple Empirical Scoring Function to Estimate the Binding Constant for a Protein-Ligand Complex of Known Three-Dimensional Structure," *J. Comput. Aided Mol. Des.*, 8(3):243-56.

Böhm, (1998), "Prediction of Binding Constants of Protein Ligands: A Fast Method for the Priorization of Hits Obtained from De Novo Design or 3D Database Search Programs," *J. Comput. Aided Mol. Des.*, 12(4):309-23.

Boshart et al., (1985), "A Very Strong Enhancer is Located Upstream of an Immediate Early Gene of Human Cytomegalovirus," *Cell*, 41:521-530.

Boulianne et al., (1984), "Production of Functional Chimeric Mouse/Human Antibody," *Nature*, 312:643-6.

Bourgois et al., (1974), "Determination of the Primary Structure of a Mouse IgG2a Immunoglobulin Amino Acid Sequence of the Fc Fragment: Implications for the Evolution of Immunoglobulin Structure and Function," *Eur. J. Biochem.*, 43:423-45.

Brambell et al., (1964), "A Theoretical Model of γ-Globulin Catabolism," *Nature*, 203:1352-55.

Brazolot Millan et al., (1998), "Cpg DNA Can Induce Strong TH1 Humoral and Cell-Mediated Immune Responses against Hepatitis B Surface Antigen in Young Mice," *Proc. Natl. Acad. Sci. USA*, 95:15553-8.

Brekke et al., (1994), "Human IgG Isotype-Specific Amino Acid Residues Affecting Complement-Mediated Cell Lysis and Phagocytosis," *Eur. J. Immunol.*, 24:2542-2547.

Brem et al., (1993), "The Combination of Antiangiogenic Agents to Inhibit Primary Tumor Growth and Metastasis," *J. Pediatr. Surg.*, 28(10):1253-7.

Brocklebank et al., (2001), "Enumeration of CD34+ Cells in Cord Blood: A Variation of a Single-Platform Flow Cytometric Method Based on the ISHAGE Gating Strategy," *Cytometry*, 46:254-261.

Brooks et al., (1983), "CHARMM: A Program for Macromolecular Energy Minimization and Dynamics Calculations," *J. Comput. Chemistry*, 4:187-217.

Broudy et al., (1988), "Recombinant Human Erythropoietin: Purification and Analysis of Carbohydrate Linkage," *Arch. Biochem. Biophys.*, 265:329-36.

Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Bumol et al., (1982), "Unique Glycoprotein-Proteoglycan Complex Defined By Monoclonal Antibody on Human Melanoma Cells," *Proc. Natl. Acad. Sci. USA*, 79:1245-9.

Carnemolla et al., (1989), "A Tumor-Associated Fibronectin Isoform Generated by Alternative Splicing of Messenger RNA Precursors," *J. Cell. Biol.*, 108:1139-1148.

Carnemolla et al., (1992), "The Inclusion of the Type III Repeat ED-B in the Fibronectin Molecule Generates Conformational Modifications that Unmask a Cryptic Sequence," *J. Biol. Chem.*, 267(34):24689-24692.

Casadevall et al., (2002) "Pure Red-Cell Aplasia and Antierythropoietin Antibodies in Patients Treated with Recombinant Erythropoietin," *The New Eng. School of Medicine*, 346:469-75.

Cazzola et al., (1998), "Red Blood Cell Precursor Mass as an Independent Determinant of Serum Erythropoietin Level," *Blood*, 91:2139-45.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and Il-2," *J. Immunol.*, 148:92-98.

Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Cheetham, (1998), "NMR Structure of Human Erythropoietin and a Comparison with its Receptor Bound Conformation," *Nat. Struct. Biol.*, 5:861-6.

Ciardiello et al., (1996), "Antitumor Activity of Combined Blockade of Epidermal Growth Factor Receptor anf Protein Kinase A," *J. Natl. Cancer Inst.*, 88:1770-6.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Congote et al., (1984), "The Erthrotropins, New Erythroid Cell Stimulate Factors Extracted From Human and Bovine Fetal Tissues," Abstract 364, "Proceedings 7th Intl. Congress of Endocrinology," Quebec City, Quebec, Jul. 1-7, 1984.

Congote, (1983), "Isolation of Two Biologically Active Peptides, Erythrotropin I and Erythrotropin II from Fetal Calf Intestine," *Biochem. Biophys. Res. Commun.*, 115(2):477-83.

Congote, (1984), "Extraction from Fetal Bovine Serum of Erythrotropin, an Erythroid Cell-Stimulating Factor," *Anal. Biochem.*, 140:428-33.

Connor et al., (2004), "Ex vivo Evaluation of Anti-EpCAM Immunocytokine huKS-IL2 in Ovarian Cancer," *J. Immunotherapy*, 27:211-219.

Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

Cunningham et al., (1989), "High-Resolution Epitope Mapping of hGH-Receptor Interactions by Alanine-Scanning Mutagenesis," *Science*, 244:1081-85.

Curiel et al., (1991), "Adenovirus Enhancement of Transferrin-Polylysine-Mediated Gene Delivery," *Proc. Natl. Acad. Sci. USA*, 88:8850-4.

Dauber-Osguthorpe et al., (1988), "Structure and Energetics of Ligand Binding to Proteins: *Escherichia coli* Dihydrofolate Reductase-Trimethoprim, A Drug-Receptor System," *Proteins*, 4:31-47.

Daugherty et al., (1991), "Polymerase Chain Reaction Facilities the Cloning, CDR-Grafting, and Rapid Expression of a Murine Monoclonal Antibody Directed Against the CD18 Component of Leukocyte Integrins," *Nucleic Acid Res.*, 19:2471-2476.

De Bruijn et al., (1995), "Phagocyte-Induced Antigen-Specific Activation of Unprimed CD8+ T Cells in Vitro," *Eur. J. Immunol.*, 25:1274-85.

Delorme et al., (1992), "Role of Glycosylation on the Secretion and Biological Activity of Erythropoietin," *Biochemistry*, 31:9871-6.

Desai et al., (1992), "IL-12 Receptor. II. Distribution and Regulation of Receptor Expression," *J. Immunol.*, 148:3125-32.

Dillman et al., (1994), "Human Anti-Mouse Antibody Response in Cancer Patients Following Single Low-Dose Injections of Radiolabeled Murine Monoclonal Antibodies," *Cancer Biotherapy*, 9:17-28.

Donnelly et al., (1993), "Targeted Delivery of Peptide Epitopes to Class I Major Histocompatibility Molecules by a Modified Pseudomonas Exotoxin," *Proc. Natl. Acad. Sci. USA*, 90:3530-4.

Donnelly et al., (1997), "DNA Vaccines," *Annu. Rev. Immunol.*, 15:617-48.

Dube et al., (1988), "Glycosylation at Specific Sites of Erythropoietin is Essential for Biosynthesis, Secretion, and Biological Function," *J. Biol. Chem.*, 263:17516-21.

Ellison et al., (1982), "The Nucleotide Sequence of a Human Immunoglobulin C $\gamma_1$ Gene," *Nucleic Acids Res.*, 10:4071-9.

Faas et al., (1993), "Phenotypically Diverse Mouse Thymic Stromal Cell Lines which Induce Proliferation and Differentiation of Hematopoietic Cells," *Eur. J. Immunol.*, 23:1201-14.

Famer et al., (1995), "Distinction Between $\gamma_c$ C Detection and Function in YT Lymphoid Cells and in the Granulocyte-Macrophage Colony-Stimulating Factor-Responsive Human Myeloid Cell Line, Tf-1," *Blood*, 86:4568-78.

Fawell et al., (1994), "Tat-Mediated Delivery of Heterologous Protein in Cells," *Proc. Natl. Acad. Sci. USA*, 91:664-8.

Fu et al., (1993), "The Sheep Erythropoietin Gene: Molecular Cloning and Effect of Hemorrhage on Plasma Erythropoietin and Renal/Liver Messenger RNA in Adult Sheep," *Mol. Cell. Endocrinol.*, 93:107-16.

Gainsford et al., (1996), "Leptin Can Induce Proliferation, Differentiation, and Functional Activation of Hemopoietic Cells," *Proc. Natl. Acad. Sci. USA*, 93:14564-14568.

Gammon et al., (1992), "Endogenous Loading of HLA-A2 Molecules with an Analog of the Influenza Virus Matrix Protein-Derived Peptide and Its Inhibition By An Exogenous Peptide Antagonist," *J. Immunol.*, 148:7-12.

Ghetie et al., (1990), "Disseminated or Localized Growth of a Human B-Cell Tumor (Daudi) in SCID Mice," *Intl. J. Cancer*, 45:485.

Ghetie et al., (1997), "FcRn: The MHC Class 1-Related Receptor that is More Than an IgG Transporter," *Immunology Today*, 18(12):592-598.

Goldwasser et al., (1971), "Purification of Erythropoietin," *Proc. Natl. Acad. Sci. USA*, 68:697-8.

Goldwasser et al., (1975), "Erythropoietin: Assay and Study of its Mode of Action," *Methods Enzymol.*, 37(PtB):109-21.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Halin et al., (2002), "Enhancement of the Antitumor Activity of Interleukin-12 by Targeted Delivery to Neovasculature," *Nature Biotechnology*, 20:264-269.

Handgretinger et al., "Immunological Aspects of Haploidentical Stem Cell Transplantation in Children," *Annals New York Academy of Sciences*, 340-(Date not known).

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Henikoff et al., (1992), "Amino Acid Substitution Matrices from Protein Blocks," *Proc. Natl. Acad. Sci. USA*, 89:10915-10919.

Hilgers et al., (1999), "Sulfolipo-Cyclodextrin in Squalane-In-Water as a Novel and Safe Vaccine Adjuvant," *Vaccine*, 17:219-28.

Hori et al., (1987), "Establishment of an Interleukin 2-Dependent Human T Cell Line from a Patient with T Cell Lymphocytic Leukemia Who is Not Infected with Human T Cell Leukemia/Lymphoma Virus," *Blood*, 70:1069-72.

Hulett et al., (1994), "Molecular Basis of Fc Receptor Function," *Adv. Immunol.*, 57:1127.

Huston et al., (1988), "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879-5883.

Investigator's Brochure 2004, pp. 6-10, 34 and 35.

Jacobs et al., (1985), "Isolation and Characterization of Genomic And cDNA Clones of Human Erythropoietin," *Nature*, 313:806-10.

Jefferis et al., (1990), "Molcular Definition of Interaction Sites on Human IgG for Fc Receptors huFcγR," *Mol. Immunol.*, 27(12):1237-1240.

Karlin et al., (1990), "Methods for Assessing the Statistical Significance of Molecular Sequence Features by Using General Scoring Schemes," *Proc. Natl. Acad. Sci. USA*, 87:2264-8.

Karlin et al., (1993), "Applications and Statistics for Multiple High-Scoring Segments in Molecular Sequences," *Proc. Natl. Acad. Sci. USA*, 90:5873-7.

Karpusas et al., (1997), "The Crystal Structure of Human Interferon β at 2.2-A Resolution," *Proc. Natl. Acad. Sci. USA*, 94:11813-11818.

Kelner et al., (1994), "Lymphotactin: A Cytokine that Represents a New Class of Chemokine," *Science*, 266:1395-9.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

King et al., (2004), "Phase I Clinical Trial of the Immunocytokine EMD 273063 in Melanoma Patients," *J. Clin. Oncol.*, 22(22):4463-73.

Klinman et al., (1997), "Contribution of CpG Motifs to the Immunogenicity of DNA Vaccines," *J. Immunol.*, 158:3635-9.

Kuntz et al., (1982), "A Geometric Approach to Macromolecule-Ligand Interactions," *J. Mol. Biol.*, 161:269-88.

Kurtz, (1982), "A New Candidate for the Regulation of Erythropoiesis. Insulin-Like Growth Factor I," *FEBLAL.*, 149(1):105-8.

Lai et al., (1986), "Structural Characterization of Human Erythropoietin," *J. Biol. Chem.*, 261:3116-21.

Lai et al., (1998), "DNA Vaccines," *Crit. Rev. Immunol.*, 18:449-84.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lawn et al., (1981), "DNA Sequence of a Major Human Leukocyte Interferon Gene," *Proc. Natl. Acad. Sci. USA*, 78:5435-9.

Lin et al., (1985), "Cloning and Expression of the Human Erythropoietin Gene," *Proc. Natl. Acad. Sci. USA*, 82:7580-4.

Lin et al., (1986), "Monkey Erythropoietin Gene: Cloning, Expression and Comparison with the Human Erythropoietin Gene," *Gene*, 44:201-9.

Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lorenz et al., (1999), "Induction of Anti-Tumor Immunity Elicited by Tumor Cells Expressing a Murine LFA-3 Analog Via a Recombinant Vaccinia Virus," *Hum. Gene Ther.*, 10:623-31.

Lotze et al., (1996), "Cytokine Gene Therapy of Cancer Using Interleukin-12: Murine and Clinical Trials," *Ann. NY Acad. Sci.*, 795:440-54.

Macdougall, et al., (2002), "Optimizing the Use of Erythropoietic Agents—Pharmacokinetics and Pharmacodynamic Considerations," *Nephol. Dial. Transplant.* 17(5):66-70.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maghazachi et al., (1997), "Interferon-Inducible Protein-10 and Lymphotactin Induce the Chemotaxis and Mobilization of Intracellular Calcium in Natural Killer Cells through Pertussis Toxin Sensitive and—Insensitive Heterotrimeric G-Proteins," *FASEB J.*, 11:765-74.

Maloy et al., (2001), "Regulatory T Cells in the Control of Immune Pathology," 2(9):816-822.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Marshall et al., (1994), "Role of the Polymorphic Residues in HLA-DR Molecules in Allele-Specific Binding of Peptide Ligands," *J. Immunol.*, 15:4946-57.

Marshall et al., (1995), "Prediction of Peptide Affinity to HLA-DR Molecules," *Biomed. Pept. Proteins Nucleic Acids*, 1(3):157-62.

Martin et al., (2001), "Crystal Structure at 2.8 A of an FcRn/Heterodimeric Fc Complex: Mechanism of pH Dependent Binding," *Molecular Cell*, 7:867-877.

McDonald, (1986), "Cloning, Sequencing, and Evolutionary Analysis of the Mouse Erythropoietin Gene," *Mol. Cell. Biol.*, 6:842-8.

McGonigle et al., (1984), "Erythropoietin Deficiency and Inhibition of Erythropoiesis in Renal Insufficiency," *Kidney Int.*, 25(2):437-44.

McMahan et al., (1991), "A Novel IL-1 Receptor, Cloned From B-Cells by Mammalian Expression is Expressed in Many Cell Types," *EMBO J.*, 10:2821-32.

McMahon et al., (1990), "Pharmacokinetics and Effects of Recombinant Human Erythropoietin after Intravenous and Subcutaneous Injections in Healthy Volunteers," *Blood*, 76:1718-22.

Mehrotra et al., (1993), "Effects of IL-12 on the Generation of Cytotoxic Activity in Human CD8+ T Lymphocytes," *J. Immunol.*, 151:2444-52.

Menard et al., (1983), "Generation of Monoclonal Antibodies Reacting with Normal and Cancer Cells of Human Breast," *Cancer Res.*, 43:1295-300.

Miyake et al., (1977), "Purification of Human Erythropoietin," *J. Biol. Chem.*, 252:5558-64.

Miyake et al., (1988), "Synthesis of Recombinant Human Single-Chain Urokinase-Type Plasminogen Activator Variants Resistant to Plasmin and Thrombin," *J. Biochem.*, 104:643-647.

Morrison et al., (1984), "Chimeric Human Antibody Molecules: Mouse Antigen-Binding Domains with Human Constant Region Domains," *Proc. Natl. Acad. Sci. USA*, 81:6851-5.

Nagao et al., (1992), "Nucleotide Sequence of Rat Erythropoietin," *Biochim. Biophys. Acta*, 1171(1):99-102.

Nastala et al., (1994), "Recombinant IL-12 Administration Induces Tumor Regression in Association with IFN-γ Production," *J. Immunol.*, 153:1697-706.

Naughton et al., (1983), "Evidence for an Erythropoietin-Stimulating Factor in Patients with Renal and Hepatic Disease," *Acta. Haemat.*, 69:171-9.

Neal et al., (2004), "Enhanced Activity of Hu14.18-IL2 Immunocytokine against Murine NXS2 Neuroblastoma when Combined with Interleukin-2 Therapy," *Clin. Cancer. Res.*, 10:4839-4847.

Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Noguchi et al., (1994), "A Mouse Mutant P53 Product Recognized by CD4+ and CD8+ T Cells," *Proc. Natl. Acad. Sci. USA*, 91:3171-5.

Orlandi et al., (1989), "Cloning Immunoglobulin Variable Domains for Expression by the Polymerase Chain Reaction," *Proc. Natl. Acad. Sci. USA*, 86:3833-7.

Palmer et al., (2001), "Phase I Study of the BLP 25 (MUCI Peptide) Liposomal Vaccine for Active Specific Immunotherapy in Stage IIIB/IV Non-Small-Cell Lung Cancer," *Clinical Lung Cancer*, 3(1):49-57.

Palucka et al., (1998), "Dendritic Cells as the Terminal Stage of Monocyte Differentiation," *J. Immunol.*, 160:4587-95.

Panina-Bordignon et al., (1989), "Universally Immunogenic T Cell Epitopes: Promiscuous Binding to Human MHC Class II and Promiscuous *Recognition* by T Cells," *Eur. J. Immunol.*, 19:2237-42.

Pavlović-Kentera et al., (1980), "Effects of Prostaglandin Synthetase Inhibitors, Salt Overload and Renomedullary Dissection on the Hypoxia Stimulated Erythropoietin Production in Rats," *Exp. Hematol.*, 8(Supp. 8):283-92.

Pedley et al. (1999), "Enhancement of Antibody-Directed Enzyme Prodrug Therapy in Colorectal Xenografts by an Antivascular Agent," *Cancer Res.*, 59:3998-4003.

Perussia et al., (1992), "Natural Killer (NK) Cell Stimulatory Factor or IL-12 Has Differential Effects on the Proliferaton of TCR-αβ+, TCR-γδ+ T Lymphocytes, and NK Cells," *J. Immunol.*, 149:3495-502.

Pluschke et al., (1996), "Molecular Cloning of a Human Melanoma-Associated Chondroitin Sulfate Proteoglycan," *Proc. Natl. Acad. Sci. USA*, 93:9710-5.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Radhakrishnan et al., (1996), "Zinc Mediated Dimer of Human Inteferon-$\alpha_{2b}$ Revealed by X-Ray Crystallography," *Structure* 4(12):1453-63.

Ramachandran et al., (1968)"Conformation of Polypeptides and Proteins," *Adv. Prot. Chem.*, 23:283-294.

Rarey et al., (1995), "Time-Efficient Docking of Flexible Ligands into Active Sites Of Proteins," *Proc. Int. Conf. Intell. Syst. Mol. Biol.* 3:300-8.

Resegotti et al., (1981), "Treatment of Aplastic Anaemia with Methenolone, Stanozolol and Nandrolone. A Report of 130 Cases," *Pan. Med.*, 23:243-8.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Rothmann et al., (1982), "Erythropoietin-Dependent Erythrocytosis associated with Hepatic Angiosarcoma," *J. Surg. Oncol.*, 20:105-8.

Runkel et al., (1998), "Structural and Functional Differences Between Glycosylated and Non-Glycosylated Forms of Human Interferon-β (IFN-β)," *Pharmaceutical Res.*, 15:641-649.

Sakano et al., (1980), "Two Types of Somatic Recombination are Necessary for the Generation of Complete Immunoglobin Heavy-Chain Genes," *Nature*, 286:676-683.

Säli et al., (1993), "Comparative Protein Modelling by Satisfaction of Spatial Restraints," *J. Mol. Biol.*, 234:779-815.

Schecter et al., (1997), "Tissue Factor is Induced by Monocyte Chemoattractant Protein-1 in Human Aortic Smooth Muscle And THP-1 Cells," *J. Biol. Chem.*, 272:28568-73.

Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.

Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Consdierable Within-Species Diversity," *Nucleic Acids Res.*, 16(17):8207-8211.

Simonsen et al., (1983), "Isolation and Expression of an Altered Mouse Dihydrofolate Reductase cDNA," *Proc. Natl. Acad. Sci. USA*, 80:2495-2499.

Smith et al., (1981), "Identification of Common Molecular Subsequences," *J. Mol. Biol.*, 147:195-197.

Soligo et al., (1998), "Expansion of Dendritic Cells Derived from Human CD34+ Cells in Static And Continuous Perfusion Cultures," *Br. J. Haematol.*, 101:352-63.

Spivak et al., (1989), "The In Vivo Metabolism of Recombinant Human Erythropoietin in the Rat," *Blood*, 73:90-9.

Stumiolo et al., (1999), "Generation of Tissue-Specific and Promiscuous HLA Ligand Databases Using DNA Microarrays and Virtual HLA Class II Matrices," *Nat. Biotech.*, 17(6):555-61.

Suliman et al., (1996), "Cloning of a cDNA Encoding Bovine Erythropoietin and Analysis of Its Transcription in Selected Tissues," *Gene*, 171:275-80.

Takahashi et al., (2000), "Immunologic Self-Tolerance Maintained by CD25+ CD+ Regulatory T Cells Constitutively Expressing Cytotoxic T Lymphocyte-Associated Antigen 4," *J. Exp. Med.*, 192(2):303-309.

Takai, (2002), "Roles of Fc Receptors in Autoimmunity," Nature, 2:580-592.

Taniguchi et al., (1980), "Expression of the Human Fibroblast Interferon Gene in *Escherichia coli*," *Proc. Natl. Acad. Sci. USA*, 77:5230-5233.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Nat. Acad. Sci. USA*, 93:250-4.

Van Den Eynde et al., (1989), "Presence on a Human Melanoma of Multiple Antigens Recognized By Autologous CTL," *Int. J. Cancer*, 44:634-40.

Van Der Bruggen et al., (1991), "A Gene Encoding an Antigen Recognized by Cytolytic T Lymphocytes on a Human Melanoma," *Science*, 254:1643-7.

Van Heyningen et al., (1982), "Human MHC Class II Molecules as Differentiation Markers," *Immunogenetics*, 16:459-69.

Voest et al., (1995), "Inhibition of Angiogenesis in Vivo by Interleukin 12," *J. Natl. Canc. Inst.*, 87:581-6.

Von Heijne et al., (1986), "A New Method for Predicting Signal Sequence Cleavage Sites," *Nucleic Acid Res.*, 14:4683-4690.

Ward et al., (1995), "The Effector Functions of Immunoglobulins: Implications for Therapy," *Therapeutic. Immunology*, 2:77-94.

Watson et al., (1984), "Compilation of Published Signal Sequences," *Nucleic Acid Res.*, 12:5145-5164.

Weitkamp et al., (1973), "Additional Data on the Population Distribution of Human Serum Albumin Genes; Three New Variants," *Ann. Hum. Genet.*, 37:219-26.

Wetzel et al., (2001), "BAY50-4798, an Interleukin-2 (IL-2) Variant, Demonstrates Selective Activation of Human and Chipanzee T Cells Relative to NK Cells but Shows Less Selectivity for T Cells from Monkeys and Rodents," *2001 ASCO Annual Meeting*.

Woof et al., (1986), "Localisation of the Monocyte-Binding Region on Human Immunoglobulin G," *Mol. Immunol.*, 23:319-30.

Wyatt et al., (1998), "The Antigenic Structure of the HIV gp120 Envelope Glycoprotein," *Nature*, 393:705-11.

Wysocka et al., (1995), "Interleukin-12 is Required for Interferon-γ Production and Lethality in Lipopolysaccharide-Induced Shock in Mice," *Eur. J. Immunol.*, 25:672-6.

Yan et al., (1996), "Characterization of an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhang et al., (1994), "Structure/Activity Analysis of Human Monocyte Chemoattractant Protein-1 (MCP-1) by Mutagenesis," *J. Biol. Chem.*, 269:15918-24.

Zhu et al., (2001), "MHC Class I-Related Neonatal Fc Receptor for IgG Is Functionally Expressed in Monocytes, Intestinal Macrophages, and Dendritic Cells," *J. Immunol.*, 166:3266-3276.

Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.

\* cited by examiner

Expression Vector Nucleotide Sequence

GTCGACATTGATTATTGACTAGTTATTAATAGTAATCAATTACGGGGTCATTAGTTCATAGCCCAT
ATATGGAGTTCCGCGTTACATAACTTACGTAAATGGCCCGCCTGGCTGACCGCCCAACGACCCCC
GCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACCTTAT
GGGACTTTCCTACTTGGCAGTACATCTACGTATTAGTCATCGCTATTACCATGGTGATGCGGTTTTG
GCAGTACATCAATGGGCGTGGATAGCGGTTTGACTCACGGGGATTTCCAAGTCTCCACCCCATTGA
CGTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCTCTGGC
TAACTACAGAACCCACTGCTTAACTGGCTTATCGAAATTAATACGACTCACTATAGGGAGACCCTC
TAGAATGAAGTTGCCTGTTAGGCTGTTGTGCTGATGTTCTGGATTCCTGGTGAGGAGAGAGGGAA
GTGAGGAGGAAATGGACAGGAGCAGGAGCACTGAATCCCATTGCTGCTCATTCCATGTATCTGGC
ATGGGTGAGAAGATGGGTCTTATCCTCCAGCATGGGGCCTCTGGGGTGAATACTTGTTAGAGGGA
GGTTCCAGATGGGAACATGTGCTATAATGTGCTATATGAAGATGCCTGGGATGTCTAAGTA
ATGCCTTAGAAGTGACTAGACACTTGCAATTCACTTTTTTGGTAAGAAGAGATTTTTAGGCTATA
AAAAATGTTATGTAAAATAACGATCACAGTTGAAATAAAAATAAAATATAAGGATGTTCATG
AATTTTGTGTATAACTATGTATTTCTCTCATTGTTCAGTTCTTCCTTAAGCGACGTGGTGATGACC
CAGACCCCCTGTCCCGTGACCCCGTGACCCGCCGAGCCCGCCCATCTCCTGCAGATCTAGTCAG
AGTCTTGTACACCGTAATGGAAACACCTATTACATTGGTACCTGCCAGAAGGCCAGGCCAGTCCA
AAGCTCCTCAAAGTTTCCAACCGATTTCTGGGGTCCCAGAGGTCAGGTTCAGTGGCAGTGGA
TCAGGGACAGATTCACACTCAAGATCAGCAGAGTGGAGGCTGAGGACCAAGCTGGGAGTTTATTCTGT
TCTCAAAGTACACATGTGTCCCGCTCGGTGCTGGGACCAAGCTATGGTGACCAAGCTGAGCTGAAACGTATT
AGTGTGTCAGGGTTCACAAGAGACTAAAGACATGTCAGCTATGTGTGTGACTAATGGTAATGTC

```
ACTAAGCTGCGGATCCCGCAATTCTAAACTCTGAGGGGTCGGATGACGTGGCCATTCTTGCCT
AAAGCATTGAGTTTACTGCAAGGTCAAGGAAAGCATGCAAAGCCCTCAGAATGCTGCAAAGAGCT
CCAACAACAAATTTAGAACTTTATTAAGGAATAGGGGAAGCTAGGAAGCTAGGAAACTCAAAACATCA
AGATTTTAAATACGCTTCTGTGTCTCCTTGCTATAATTATCTGGATAAGCATGCTGTTTTCTGTCT
GTCCCTAACATGCCCCTGTGATTATCGCAAACAACACACCAAGGCAGAACTTGTGTTACTTAAAC
ACCATCCTGTTTGCTTCTTCCAGGAACTGGCTGCACCATCTGTCTTCATCTTCCCGCCATCTG
ATGAGCAGTTGAAATCTGGAAATGCCCTCTGTTGTGTGCCTGCTGAATAACTTCTATCCAGAGAGG
CCAAAGTACAGTGGAAGGTGATAACGCCCTCCAATGGGTACTCCCAGGAGAGTGTCACAGAG
CAGGACAAGCAAGCACACTACAGCCTCAGCAGCACCCATCAGGGCCTGAGCTCGCCCGTCACAAAGAGC
AGAAACACAAAGTCTACGCCTGCGAAGTCACCCATCAGGGCCTGAGCTCGCCCGTCACAAAGAGC
TTCAACAGGGGAGAGTGTTAGAGGGAGAAGTGCCCCACCCTGCTCCCTCAGTTCCAGCCTGACCCCC
TCCCATCCTTTGGCCTCTGACCCTTTTCCACAGGGACCTACCCCTATTGCGGTCCTCCAGCTCAT
CTTCACCTCACCCCCCTCCCCTGGCTTTAATTATGCTAATATGTGGAGAATGAATAAT
AAGTGAATCTTTGCACCTGGTTCTCTCTCCTCAATTAATTAATATATCGTGTTGTTTACCA
ACTACTCAATTTCTCATTCTATTTACCTAAATATGTAGTCATCTCGAAGACAGTCCTCAAACCATTATAAA
AATCATCCTCTCATTCTATTTACCCTAAATATGTAGTCATCTCTGAAGACAGTCCTCCCTCAAACCCACAAGCC
TTCTGTCTCACAGTCCTTTACACCTGGTAGGGTACAGGTCTTACGGTCATATATCCTTTGATTCAATTCCCTGG
AGCCCTCATAGTCCTTTAAGGGTGACAGGTCTTACGGTCATATATCCTTTGATTCAATTCCCTGG
GAATCAACCAAGGCAAATTTTCAAAAGAACACAATAAAGAAACCTGTATAAAGAGAATCATTGCAACA
TGATATAAATAACACACAATAATGAATGTCATGCCTTATTTACATTTTTAAACAGGTACTGAGGAC
ATCATGGTACTTAGACTTAATGAATGTCATGCCTTATTTACATTTTTAAACAGGTACTGAGGAC
TCCTGTCTGCCAAGGCCGTATTGAGTACTTTCAAAGGTTCTATAAAGCTGAGAGACAATATATTCTATAC
ATTAAAACATCCCACTTCATTAAAATGTGCAAATGTGACTTCAAAGGTTCTATAAAGCTGAGAGACAATATATTCTATAC
TCAGCAATCCCACTTCTAGGGTCGATCGACGTTGACATTGATTATTGACTAGTTGATTATTAATAGTAATC
AATTACGGGGTCATTAGTTCATAGCCCATATGGAGTTCCGCGTTACATAACTTACGGTAAATGG
CCGCCTGGCTGACCGCCAAGCACGACCCCGCCATTGACGTCAATAATGACGTATGTTCCCATAGT
AACGCCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGACGGTAAATGGCCCGC
```

```
CTGGCATTATGCCCAGTACACATGACCTTATGGGACTTTCCTACTTGGCAGTACATCTACGTATTAGTC
ATCGCTATTACCATGGTGATGCGGTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGG
GACTTTCCAAAATGTCGTAACAACTCCGCCCCATTGACGCAAATGGGCGGTAGGCGTGTACGGTG
GGAGGTCTATATAAGCAGAGCTCTCTGGCTAACTACAGAACCCACTGCTTAACTGGCTTATCGAAA
TAATACGACTCACTATAGGGAGACCCAAGCTCCTGAGGCTAGAATGAAGTTGCCTGTTAGGCTG
TTGGTGCTGATGTTCTGGATTCCTGGTGAGGAGAAGTGAGGGAAGTGAGGAGAATGGACAGGGA
GCAGGAGCACTACTGAATCCCATTGCTCATTCCATGTATCTGGCATGGGTGAGAAGATGGGTCTTATCC
TCCAGCATGGGCCTCTGGGGTGAATACTTGTTAGAGGGAGGTTCCAGATGGGAACATGTCTAT
AATGAAGATTATGAACTCTAAGTAATGCCTTAGAAGTGACTAGACACTT
GCAATTCACTTTTTGTAAGAAGAGATTTTTAGGCTATAAAAATGTTATGTAAAATAAACG
ATCACAGTTGAAATAAAAATAAGGATGTTCATGAATTTGTGTATAACTATGTATTTCT
CTCTCATTGTTCAGCTTCCTTAAGCGAGGTGCAGTGCAGTCCGAGGTGGAGAAGC
CCGGCCCTCCGTGAAGATCTCCTGCAAGGCTCTGAAACATGAACT
GGGTGGCGCAGGCCAGAACACTGGCAAGTCCCTGGAGTCCATGGATCGGCTACGGGGC
ACCTCCTACAACCAGAAGTTCAAGGGGCGCCACCCTGACCGTGACAAGTCCACCTCCACCGC
CTACATGCACCTGAAGTCCCTGCGCTCCGAGGACACCGCCGTGTACTACTGCGTGTCCGGCATGA
GTACTGGGCCAGGGCACCCTGACCGTCTCCTCCGGTAAGCTTTCTGGGCAGGCCAGGCCT
GACCTTGGCTTTGGGAGCCCAGCTCAAGCCTCCAGAGAGGCCAGGCCAGGTGCACACCC
AATGCCCATGAGCCCAGACACTCTGGACGCTGAACCTCGCGGACAGTTAAGAACCAGGGCCTCTG
CGCCCTGGGCCCAGTCTGTTTCCCCTGGCCACCACGGTCACACCACCTCTTGCAGCCTCCACCA
AGGGCCCATGGTCCTGTCAAGGACTACTTCCCCGAACCGGTGACGGTGTCGTGGAACTCAGGCGCTGG
GCTGCCTGGTCAAGGACTACTTCCCCGAACCGGTGACGGTGTCGTGGAACTCAGGCGCCCTGACCA
GCGGCGTGCACACCTTCCCGGCTGTCCTACAGTCCTCAGGACTCTACTCCCTCAGCAGCGTGGTGA
```

FIG. 2C

```
CCGTGCCCTCCAGCAGCTTGGGCACCCAGACCTACATCTGCAACGTGAATCACAAGCCCAGCAAC
ACCAAGGTGGACAAGAGAGTTGGTGAGAGGCCAGCACAGGGAGGAGGTGTCTGCTGGAAGCC
AGGCTCAGCGCTCCTGACGGCATCCCGGCTCAGTCCCAGTCCAGGCAGCAAGGCAGG
CCCGTCGCCTCTCTTCACCCGGAGCCTGCCGCCCACTCATGCTCAGGAGAGGGTCTCTG
GCTTTTTCCCCAGGCTCTGGGCAGGCACAGGCTAGGTGCCCCTAACCCAGCCCTGCACACAAGG
GGCAGGTGCTGGCTCAGAGACCTGCCAAGAGCCATATCCGGGAGACCCTGCCCCTGACCTAAGCC
CACCCCAAAGGCCAAACTCTCCACTCCTCAGTCTGGACACCTTCTCTCCCAGATTCCAGTAA
CTCCCAATCTCTCTGCAGAGCCCTCCAGTCAGCCCAAATCTTGTGACAAAACTCACACATGCCCCAG
GTAAGCCAGCAGGCCCTCGCCTCCAGTCAGGCGGACAGGTGCCTAGAGTAGCCTGCATC
CAGGGACAGGCCCCAGCCCGGTCAGTCTCTCCTTGCGACACGTCCACCTCAGCACCTGAACTCCT
GGGGGGACCGTCAGTCTCCTCTCCCCCAAAACCCAAGGACACCCTCATGATCTCCGACCCC
TGAGGTCACATGCGTGGAGGTGCATAATGCCAAGACACAAAGCCGCGGGAGGAGCAGTACAACAGCACGTA
TGGACGGGCGTGGAGGTCCTCAGCGTCCTCCACGCCCTCGAGGTGCTGAATGGCAAGGAGTACAAGTGCA
CCGTGTGGTCAGCGTCCTCCACCGTCCTGCAAGACAAAGCCGGACTGCTGAATGGCAAGGAGTACAAGTGCA
AGGTCTCCAACAAAGCCCTCCCAGCCCCCATCGAGAAAACCATCTCCAAAGCCAAAGGGTGGGACC
CGTGGGGTGCGAGGGCCACATGGACACAGAGGCCGGGAGAACCACAGGTGTACACCCTGCCCCCATCCC
CTGTACCAACCTCTGTCCCTACAGAACCAAGGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCT
GGACTCCGACGGCTCCTTCTTCCTCTATAGCAAGCTCACCGTGGACAAGAGCAGGTGGCAGCAGG
GGAACGTCTTCTCATGCTCCGTGATGCATGAGGCTCTGCACAACCACTACACGCAGAAGAGCCTCT
CCCTGTCTCCCGGGTAAAGCCCAACTTCTACAGGTTCTACAGTTCTACAAGTTCTACAAGTCAACTGAGCAT
CTCCTGCTGGATCCCAGATGATTCTACATGCTCAAGTTCTGAATGCCCAAGAAGGCCACAGAATCCAAACTCACCAGG
ATGCTCACATTCAAGTTCTACACGGAGAAGGCTAAACCTCGCTCAGACTAAGTTCTGAACTAAGTTCTGAACTAAGTTCTGAAGGATCCGAAACATTCA
TAGGGACTTAATCAGCAATATCAACGTAATAGTTCTGAACTAAAGGGATCCGAAACATTCA
TGTGTGAATATGCTGATGAGAGACAGCAACCATTGTAGAATTTCTGAACAGATGGATTACCTTTGTC
```

FIG. 2D

AAAGCATCATCTCAACACTAACTTGATAATTAAGTGTCTCGAGGGATCCAGACATGATAAGATACA
TTGATGAGTTTGACAAACCACAACTAGAATGCAGTAGAAAAAATGCTTTATTTGTGAAATTGTG
ATGCTATTGCTTTATTTGTAACCATTAGAAGCTGCAATAAACAAGTTAACAACAATTGCATTC
ATTTATGTTTCAGGTTCAGGGGAGGTGTGGAGGTTTTTAAAGCAAGTAAAACCTCTACAAAT
GTGGTATGGCTGATTATGATCCTGCCTCGCCGCGTTGTCTGTAAGCGGATGACGGTGAAAACCTCTGACACAT
GCAGCTCCCGGAGACGGTCACAGTTGTCTGTGGGCGCAGCCATGACCCAGTCACGTAGCGGA
GCGCGTCAGCGGGTGTTGGCGGTGTCGGGGCGCAGCAGATTGTACTGAGAGTGCACCATATGCGGTGTG
GTGTATACTGGCTTAACTATGCGGTAAGGAGAAAATACCGCATCAGAGCAGATTGTACTCAGGCGCTCTTCCGCTCACTG
AAATACCGCACAGATGCGTAAGGAGAAAATACCGCATCAGAGCAGATTGTACTCAGGCGCTCTTCCGCTCACTG
ACTCGCTGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATACCTGTCCGCCTTTCT
CCCTTCGGGAAGCGTGGCGCTTTCTCAATGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGGAAAAGAGTTGG
TAGCTCTTGATCCGGCAAACAACCACCGCTGGTAGCGGTGGTTTTTTTGTTTGCAAGCAGCAGAT
TACGCGCAGAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAGGATCTTCACCTAGATCCT

FIG. 2E

TTTAAATTAAAAATGAAGTTTAAATCAATCTAAAGTATATGAGTAAACTTGGTCTGACAGTTA
CCAATGCTTAATCAGTGAGGCACCTATCTCAGCGATCTGTCTATTTGTTCATCCATAGTGCCTGA
CTCCCCGTCGTGTAGATAACTACGATACGGGAGGGCTTACCATCTGGCCCCAGTGCTGCAATGATA
CGGCGAGACCCACGCTCACCGGCTCCAGATTTATCAGCAATAAACCAGCCAGCCGGAAGGGCGA
GCGCAGAAGTGGTCCTGCAACTTTATCCGCCTCCAGTCGCTCTATTAATTGTTGCGGGAAGCTAG
AGTAAGTAGTTCGGCCAGTAGTTTGGCAACGTTGTTGCCATTGCTGCAGGCATCGTGGTGTC
ACGCTCGTCGTTTGGTATGGCTTCATTCAGTGCTCCAACGATCAAGGCGAGTTACATGATC
CCCCATGTTGTGCAAAAAGCGGTTAGCTGTCCTCCGATCGTGTCAGAAGTAAGTTGGC
GCAGTGTTATCACTCATGGTTGAGTACTCAACCAAGTCATTCTCTACTGTCATGCCATCCGTAAGA
TGCTTTTCTGTGACTGGTGAGTACTCAACCAAGTCATTCTCTGAGAATAGTGTATGCGGCGACCGAGT
TGCTCTTGCCGGTCAACACGGGATAATACCGCGCCACATAGCAGAACTTAAAGTGCTCATC
ATTGGAAAACGTTCTTCGGGGCGAAAACTCTCAAGGATCTTACTTTACCAGCGTTTCTGGGTGAGCAA
TAACCCACTCGTGCACCCAACTGATCTTCAGCATCTTTTACTTCACCAGCGTTTCTGGGTGAGCAA
AAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTT
GAATGTATTTAGAAAAATAAACAAATAGGGGTTCCGCGCACATTTCCCCCGAAAAGTGCCACCTGA
CGTCTAAGAAACCATTATTATCATGACATTAACCTATAAAAATAGGCGTATCACGAGGCCCTTTCG
TCTTCAAGAATTCAAAAAATGCTTTATTGTGAAATTGTTATCGGCTATTGCTTCATTTGTAACCATTAGAA
ATGCAGTGAAAAAAATGCTTTATTGTGAAATTGTTATCGGCTATTGCTTCATTTGTAACCATTAGAA
GCTGCAATAAACAAGTTAACAACAACAATTGCATTCATTTTATGTTTCAGGTTCAGGGGGAGGTGT
GGGAGGTTTTTTAAAGCAAGTAAAACCTCTACAAATGTGGTATGGCTGATTATGATCTAAAGCCAG
CAAAAGTCCCATGGTCTTATCTCTCGAGACATAGCTTTCCTTTCCTCTGACCTCAG
TTCCTGTTAGTCTTTCTCTGGGTATTCTGCATGATCCGTGTACTTGTCACAAAGAGTCCTTGAGGTCTGGCCTGTTGATTCATGGCTTC
AGAGGACGCCATGGTCTTATCTCTCGAGACATAGCTTTCCTTTCCTCTGACCTCAG
CACTTTCAAATTCCTGCATGATCCGTGTACTTGTCACAAAGAGTCCTTGAGGTCTGGTTGATTCATGGCTTC
CTGGTAAACAGAACTGCCTCGACTATCCAAAACCATGTACTTACTTGCCAATTCCGGTTGTTCA
ATAAGTCTTAAGGCATCATCCAAACTTTGGCAAGAAAATGAGCTCCTGTCGTGTCTTTGAGT
TCTCTACTGAGAACTATATTAATTCTGTCCTTAAGGTCGATTCTCTCAGGAATGGAGAACCAG

FIG. 2F

GTTTCCTACCCATAATCACCAGATTCTGTTTACCTTCCACTGAAGAGGTTGTGTCATTCTTTGGA
AGTACTTGAACTCGTTCCTGAGCGGAGGCCAGGGTCTCCGTTCTGCCAATCCCCATATTTTG
GGACACGGCGACGATGCAGTTCAATGGTCGAACCATGAGGGCACCAAGCTAGCTTTTGCAAAAG
CCTAGGCCTCCAAAAGCCTCCTCACTACTTCTGAATAGCTCAGAGGCCCGAGGCGGCCTCGGCC
TCTGCATAAATAAAAAAAATTAGTCAGCCATGGGGCGGAGAATGGGCGGAACTGGGCGGAGTTAG
GGGCGGGATGGGCGGAGTTAGGGGCGGGACTATGGTTGCTGACTAATTGAGATGCATGCTTTGCA
TACTTCTGCCTGGTCTGGGGAGCCTGGGACTTTCCACACCTGGTTGCTGACTAATTGAGATGCATGC
TTTGCATACTTCTGCCTGCTGGGGGAGCCTGGGACTTTCCACACCCTAACTGACACACATTCCACA (SEQ ID NO: 4)

FIG. 2G

Humanized Immunoglobulin Light Chain

D-V-V-M-T-Q-T-P-L-S-L-P-V-T-P-G-E-P-A-S-I-S-C-R-S-S-Q-S-L-V-H-R-N-G-N-T-Y-

L-H-W-Y-L-Q-K-P-G-Q-S-P-K-L-L-I-H-K-V-S-N-R-F-S-G-V-P-D-R-F-S-G-S-G-S-G-T-

D-F-T-L-K-I-S-R-V-E-A-E-D-L-G-V-Y-F-C-S-Q-S-T-H-V-P-P-L-T-F-G-A-G-T-K-L-E-

L-K-R-T-V-A-A-P-S-V-F-I-F-P-P-S-D-E-Q-L-K-S-G-T-A-S-V-V-C-L-L-N-N-F-Y-P-R-

E-A-K-V-Q-W-K-V-D-N-A-L-Q-S-G-N-S-Q-E-S-V-T-E-Q-D-S-K-D-S-T-Y-S-L-S-S-T-

L-T-L-S-K-A-D-Y-E-K-H-K-V-Y-A-C-E-V-T-H-Q-G-L-S-S-P-V-T-K-S-F-N-R-G-E-C (SEQ ID NO: 5)

FIG. 3A

Humanized Immunoglobulin Heavy Chain-IL-2

E-V-Q-L-V-Q-S-G-A-E-V-E-K-P-G-A-S-V-K-I-S-C-K-A-S-G-S-S-F-T-G-Y-N-M-N-W-V-R-Q-N-I-G-K-S-L-E-W-I-G-
A-I-D-P-Y-Y-G-G-T-S-Y-N-Q-K-F-K-G-R-A-T-L-T-V-D-K-S-T-S-T-A-Y-M-H-L-K-S-L-R-S-E-D-T-A-V-Y-Y-C-V-S-

G-M-E-Y-W-G-Q-G-T-S-V-T-V-S-S-A-S-T-K-G-P-S-V-F-P-L-A-P-S-S-K-S-T-S-G-G-T-A-A-L-G-C-L-V-K-D-Y-F-P-

E-P-V-T-V-S-W-N-S-G-A-L-T-S-G-V-H-T-F-P-A-V-L-Q-S-S-G-L-Y-S-L-S-S-V-V-T-V-P-S-S-S-L-G-T-Q-T-Y-I-C-N-

V-N-H-K-P-S-N-T-K-V-D-K-R-V-E-P-K-S-C-D-K-T-H-T-C-P-P-C-P-A-P-E-L-L-G-G-P-S-V-F-L-F-P-P-K-P-K-D-T-L-

M-I-S-R-T-P-E-V-T-C-V-V-V-D-V-S-H-E-D-P-E-V-K-F-N-W-Y-V-D-G-V-E-V-H-N-A-K-T-K-P-R-E-E-Q-Y-N-S-T-Y-

R-V-V-S-V-L-T-V-L-H-Q-D-W-L-N-G-K-E-Y-K-C-K-V-S-N-K-A-L-P-A-P-I-E-K-T-I-S-K-A-K-G-Q-P-R-E-P-Q-V-Y-

T-L-P-P-S-R-E-E-M-T-K-N-Q-V-S-L-T-C-L-V-K-G-F-Y-P-S-D-I-A-V-E-W-E-S-N-G-Q-P-E-N-N-Y-K-T-T-P-P-V-L-D-

S-D-G-S-F-F-L-Y-S-K-L-T-V-D-K-S-R-W-Q-Q-G-N-V-F-S-C-S-V-M-H-E-A-L-H-N-H-Y-T-Q-K-S-L-S-L-S-P-G-A-P-

T-S-S-S-T-K-K-T-Q-L-Q-L-E-H-L-L-L-D-L-Q-M-I-L-N-G-I-N-N-Y-K-N-P-K-L-T-R-M-L-T-F-K-F-Y-M-P-K-K-A-T-

E-L-K-H-L-Q-C-L-E-E-E-L-K-P-L-E-E-V-L-N-L-A-Q-S-K-N-F-H-L-R-P-R-D-L-I-S-N-I-N-V-I-V-L-E-L-K-G-S-E-T-T-

F-M-C-E-Y-A-D-E-T-A-T-I-V-E-F-L-N-R-W-I-T-F-C-Q-S-I-I-S-T-L-T (SEQ ID NO: 6)

FIG. 3B

SEQUENCE LISTING

```
<160> NUMBER OF SEQ ID NOS: 6

<210> SEQ ID NO 1
<211> LENGTH: 113
<212> TYPE: PRT
<213> ORGANISM: Artificial Sequence
<220> FEATURE:
<223> OTHER INFORMATION: Humanized Immunoglobulin Light Chain Variable
      Region

<400> SEQUENCE: 1

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

-continued

Ser Arg Val Glu Ala Glu Asp Leu Gly Val Tyr Phe Cys Ser Gln Ser
             85                  90                  95

Thr His Val Pro Pro Leu Thr Phe Gly Ala Gly Thr Lys Leu Glu Leu
        100                 105                 110

Lys

<210> SEQ ID NO 2
<211> LENGTH: 113
<212> TYPE: PRT
<213> ORGANISM: Artificial Sequence
<220> FEATURE:
<223> OTHER INFORMATION: Humanized Immunoglobulin Heavy Chain Variable
      Region

<400> SEQUENCE: 2

Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
                85                  90                  95

Val Ser Gly Met Glu Tyr Trp Gly Gln Gly Thr Ser Val Thr Val Ser
            100                 105                 110

Ser

<210> SEQ ID NO 3
<211> LENGTH: 15
<212> TYPE: PRT
<213> ORGANISM: Artificial Sequence
<220> FEATURE:
<223> OTHER INFORMATION: Linker sequence

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 10531
<212> TYPE: DNA
<213> ORGANISM: Artificial Sequence
<220> FEATURE:
<223> OTHER INFORMATION: Vector containing humanized immunoglobulin
      light and heavy chain and IL-2

<400> SEQUENCE: 4
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420

-continued

| | |
|---|---|
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctctc tggctaacta | 600 |
| cagaacccac tgcttaactg gcttatcgaa attaatacga ctcactatag ggagaccctc | 660 |
| tagaatgaag ttgcctgtta ggctgttggt gctgatgttc tggattcctg gtgaggagag | 720 |
| agggaagtga gggaggagaa tggacaggga gcaggagcac tgaatcccat tgctcattcc | 780 |
| atgtatctgg catgggtgag aagatgggtc ttatcctcca gcatgggcc tctggggtga | 840 |
| atacttgtta gagggaggtt ccagatggga acatgtgcta atgaagat tatgaaatgg | 900 |
| atgcctggga tggtctaagt aatgccttag aagtgactag acacttgcaa ttcactttt | 960 |
| ttggtaagaa gagatttta ggctataaaa aaatgttatg taaaaataaa cgatcacagt | 1020 |
| tgaaataaaa aaaaaatata aggatgttca tgaattttgt gtataactat gtatttctct | 1080 |
| ctcattgttt cagcttcctt aagcgacgtg gtgatgaccc agacccccct gtccctgccc | 1140 |
| gtgaccccg gcgagcccgc ctccatctcc tgcagatcta gtcagagtct tgtacaccgt | 1200 |
| aatggaaaca cctatttaca ttggtacctg cagaagccag gccagtctcc aaagctcctg | 1260 |
| attcacaaag tttccaaccg attttctggg gtcccagaca ggttcagtgg cagtggatca | 1320 |
| gggacagatt tcacactcaa gatcagcaga gtggaggctg aggatctggg agtttatttc | 1380 |
| tgttctcaaa gtacacatgt tcctccgctc acgttcggtg ctgggaccaa gctggagctg | 1440 |
| aaacgtatta gtgtgtcagg gtttcacaag agggactaaa gacatgtcag ctatgtgtga | 1500 |
| ctaatggtaa tgtcactaag ctgcgggatc ccgcaattct aaactctgag ggggtcggat | 1560 |
| gacgtggcca ttcttttgcct aaagcattga gtttactgca aggtcagaaa agcatgcaaa | 1620 |
| gccctcagaa tggctgcaaa gagctccaac aaaacaattt agaactttat taaggaatag | 1680 |
| ggggaagcta ggaagaaact caaaacatca agattttaaa tacgcttctt ggtctccttg | 1740 |
| ctataattat ctgggataag catgctgttt tctgtctgtc cctaacatgc cctgtgatta | 1800 |
| tccgcaaaca acacacccaa gggcagaact ttgttactta acaccatcc tgtttgcttc | 1860 |
| tttcctcagg aactgtggct gcaccatctg tcttcatctt cccgccatct gatgagcagt | 1920 |
| tgaaatctgg aactgcctct gttgtgtgcc tgctgaataa cttctatccc agagaggcca | 1980 |
| aagtacagtg gaaggtggat aacgccctcc aatcgggtaa ctcccaggag agtgtcacag | 2040 |
| agcaggacag caaggacagc acctacagcc tcagcagcac cctgacgctg agcaaagcag | 2100 |
| actacgagaa acacaaagtc tacgcctgcg aagtcaccca tcagggcctg agctcgcccg | 2160 |
| tcacaaagag cttcaacagg ggagagtgtt agagggagaa gtgccccac ctgctcctca | 2220 |
| gttccagcct gaccccctcc catcctttgg cctctgaccc ttttccaca ggggacctac | 2280 |
| ccctattgcg gtcctccagc tcatctttca cctcaccccc ctcctcctcc ttggctttaa | 2340 |
| ttatgctaat gttggaggag aatgaataaa taaagtgaat ctttgcacct gtggtttctc | 2400 |
| tctttcctca atttaataat tattatctgt gtttaccaa ctactcaatt tctcttataa | 2460 |
| gggactaaat atgtagtcat cctaaggcgc ataaccattt ataaaatca tccttcattc | 2520 |
| tattttacc tatcatcctc tgcaagacag tcctccctca aacccacaag ccttctgtcc | 2580 |
| tcacagtccc ctgggccatg gtaggagaga cttgcttcct tgttttcccc tcctcagcaa | 2640 |
| gcccctcatag tccttttta gggtgacagg tcttacggtc atatatcctt tgattcaatt | 2700 |
| ccctgggaat caaccaaggc aaattttca aagaagaaa cctgctataa agagaatcat | 2760 |

-continued

```
tcattgcaac atgatataaa ataacaacac aataaaagca attaaataaa caaacaatag    2820
ggaaatgttt aagttcatca tggtacttag acttaatgga atgtcatgcc ttatttacat    2880
ttttaaacag gtactgaggg actcctgtct gccaagggcc gtattgagta ctttccacaa    2940
cctaatttaa tccacactat actgtgagat taaaaacatt cattaaaatg ttgcaaaggt    3000
tctataaagc tgagagacaa atatattcta taactcagca atcccacttc tagggtcgat    3060
cgacgttgac attgattatt gactagttat taatagtaat caattacggg gtcattagtt    3120
catagcccat atatggagtt ccgcgttaca taacttacgg taaatggccc gcctggctga    3180
ccgcccaacg acccccgccc attgacgtca ataatgacgt atgttcccat agtaacgcca    3240
atagggactt tccattgacg tcaatgggtg gagtatttac ggtaaactgc ccacttggca    3300
gtacatcaag tgtatcatat gccaagtacg cccctattg acgtcaatga cggtaaatgg    3360
cccgcctggc attatgccca gtacatgacc ttatgggact ttcctacttg gcagtacatc    3420
tacgtattag tcatcgctat taccatggtg atgcggtttt ggcagtacat caatgggcgt    3480
ggatagcggt ttgactcacg gggatttcca agtctccacc ccattgacgt caatgggagt    3540
ttgttttggc accaaaatca acgggacttt ccaaaatgtc gtaacaactc cgccccattg    3600
acgcaaatgg gcggtaggcg tgtacggtgg gaggtctata taagcagagc tctctggcta    3660
actacagaac ccactgctta actggcttat cgaaattaat acgactcact atagggagac    3720
ccaagctcct cgaggctaga atgaagttgc ctgttaggct gttggtgctg atgttctgga    3780
ttcctggtga ggagagaggg aagtgaggga ggagaatgga cagggagcag gagcactgaa    3840
tcccattgct cattccatgt atctggcatg ggtgagaaga tgggtcttat cctccagcat    3900
ggggcctctg gggtgaatac ttgttagagg gaggttccag atgggaacat gtgctataat    3960
gaagattatg aaatggatgc ctgggatggt ctaagtaatg ccttagaagt gactagacac    4020
ttgcaattca cttttttttgg taagaagaga ttttttaggct ataaaaaaat gttatgtaaa    4080
aataaacgat cacagttgaa ataaaaaaaa aatataagga tgttcatgaa ttttgtgtat    4140
aactatgtat ttctctctca ttgtttcagc ttccttaagc gaggtgcagc tggtgcagtc    4200
cggcgccgag gtggagaagc ccggcgcctc cgtgaagatc tcctgcaagg cctccggctc    4260
ctccttcacc ggctacaaca tgaactgggt gcgccagaac atcggcaagt ccctggagtg    4320
gatcggcgcc atcgaccct actacggcgg cacctcctac aaccagaagt tcaagggccg    4380
cgccaccctg accgtggaca gtccacctc accgcctac atgcacctga gtccctgcg    4440 ctccgaggac accgccgtgt actactgcgt gtccggcatg gagtactggg gccagggcac    4500
ctccgtgacc gtgtcctccg gtaagctttt ctggggcagg ccaggcctga ccttggcttt    4560
ggggcaggga gggggctaag gtgaggcagg tggcgccagc caggtgcaca cccaatgccc    4620
atgagcccag acactggacg ctgaacctcg cggacagtta agaacccagg ggcctctgcg    4680
ccctgggccc agctctgtcc cacaccgcgg tcacatggca ccacctctct gcagcctcc    4740 accaagggcc catcggtctt ccccctggca ccctcctcca agagcacctc tgggggcaca    4800
gcggccctgg gctgcctggt caaggactac ttccccgaac cggtgacggt gtcgtggaac    4860
tcaggcgccc tgaccagcgg cgtgcacacc ttcccggctg tcctacagtc ctcaggactc    4920
tactccctca gcagcgtggt gaccgtgccc tccagcagct gggcaccca gacctacatc    4980 tgcaacgtga atcacaagcc cagcaacacc aaggtggaca agagagttgg tgagaggcca    5040
gcacagggag ggagggtgtc tgctggaagc caggctcagc gctcctgcct ggacgcatcc    5100
cggctatgca gtcccagtcc agggcagcaa ggcaggcccc gtctgcctct tcacccggag    5160
```

-continued

```
gcctctgccc gccccactca tgctcaggga gagggtcttc tggctttttc cccaggctct   5220
gggcaggcac aggctaggtg cccctaaccc aggccctgca cacaaagggg caggtgctgg   5280
gctcagacct gccaagagcc atatccggga ggacctgcc cctgacctaa gcccaccca    5340 aaggccaaac tctccactcc ctcagctcgg acaccttctc tcctcccaga ttccagtaac   5400
tcccaatctt ctctctgcag agcccaaatc ttgtgacaaa actcacacat gcccaccgtg   5460
cccaggtaag ccagcccagg cctcgccctc agctcaagg cgggacaggt gccctagagt   5520
agcctgcatc cagggacagg ccccagccgg gtgctgacac gtccacctcc atctcttcct   5580
cagcacctga actcctgggg ggaccgtcag tcttcctctt ccccccaaaa cccaaggaca   5640
ccctcatgat ctcccggacc cctgaggtca catgcgtggt ggtggacgtg agccacgaag   5700
accctgaggt caagttcaac tggtacgtgg acggcgtgga ggtgcataat gccaagacaa   5760
agccgcggga ggagcagtac aacagcacgt accgtgtggt cagcgtcctc accgtcctgc   5820
accaggactg gctgaatggc aaggagtaca agtgcaaggt ctccaacaaa gccctcccag   5880
cccccatcga gaaaaccatc tccaaagcca aggtgggac ccgtggggtg cgagggccac   5940
atggacagag gccggctcgg cccaccctct gccctgagag tgaccgctgt accaacctct   6000
gtccctacag ggcagccccg agaaccacag gtgtacaccc tgcccccatc acgggaggag   6060
atgaccaaga accaggtcag cctgacctgc ctggtcaaag gcttctatcc cagcgacatc   6120
gccgtggagt gggagagcaa tgggcagccg gagaacaact acaagaccac gcctcccgtg   6180
ctggactccg acggctcctt cttcctctat agcaagctca ccgtggacaa gagcaggtgg   6240
cagcagggga acgtcttctc atgctccgtg atgcatgagg ctctgcacaa ccactacacg   6300
cagaagagcc tctccctgtc cccgggtaaa gccccaactt caagttctac aaagaaaaca   6360
cagctgcaac tggagcatct cctgctggat ctccagatga ttctgaatgg aattaacaac   6420
tacaagaatc ccaaactcac caggatgctc acattcaagt ctacatgcc caagaaggcc    6480 acagagctca acatctcca gtgtctagag gaggaactca aacctctgga ggaagtgcta   6540
aacctcgctc agagcaaaaa cttccactta agacctaggg acttaatcag caatatcaac   6600
gtaatagttc tggaactaaa gggatccgaa acaacattca tgtgtgaata tgctgatgag   6660
acagcaacca ttgtagaatt tctgaacaga tggattacct tttgtcaaag catcatctca   6720
acactaactt gataattaag tgctcgaggg atccagacat gataagatac attgatgagt   6780
ttggacaaac cacaactaga atgcagtgaa aaaaatgctt tatttgtgaa atttgtgatg   6840
ctattgcttt atttgtaacc attagaagct gcaataaaca agttaacaac aacaattgca   6900
ttcattttat gtttcaggtt caggggagg tgtgggaggt tttttaaagc aagtaaaacc   6960
tctacaaatg tggtatggct gattatgatc ctgcctcgcg cgtttcggtg atgacggtga   7020
aaacctctga cacatgcagc tcccggagac ggtcacagct tgtctgtaag cggatgccgg   7080
gagcagacaa gcccgtcagg gcgcgtcagc gggtgttggc gggtgtcggg gcgcagccat   7140
gacccagtca cgtagcgata gcggagtgta tactggctta actatgcggc atcagagcag   7200
attgtactga gagtgcacca tatgcggtgt gaaataccgc acagatgcgt aaggagaaaa   7260
taccgcatca ggcgctcttc cgcttcctcg ctcactgact cgctgcgctc ggtcgttcgg   7320
ctgcggcgag cggtatcagc tcactcaaag gcggtaatac ggttatccac agaatcaggg   7380
gataacgcag gaaagaacat gtgagcaaaa ggccagcaaa aggccaggaa ccgtaaaaag   7440
gccgcgttgc tggcgttttt ccataggctc cgcccccctg acgagcatca caaaaatcga   7500
```

-continued

```
cgctcaagtc agaggtggcg aaacccgaca ggactataaa gataccaggc gtttccccct    7560
ggaagctccc tcgtgcgctc tcctgttccg accctgccgc ttaccggata cctgtccgcc    7620
tttctccctt cgggaagcgt ggcgctttct caatgctcac gctgtaggta tctcagttcg    7680
gtgtaggtcg ttcgctccaa gctgggctgt gtgcacgaac cccccgttca gcccgaccgc    7740
tgcgccttat ccggtaacta tcgtcttgag tccaacccgg taagacacga cttatcgcca    7800
ctggcagcag ccactggtaa caggattagc agagcgaggt atgtaggcgg tgctacagag    7860
ttcttgaagt ggtggcctaa ctacggctac actagaagga cagtatttgg tatctgcgct    7920
ctgctgaagc cagttacctt cggaaaaaga gttggtagct cttgatccgg caaacaaacc    7980
accgctggta gcggtggttt ttttgtttgc aagcagcaga ttacgcgcag aaaaaagga    8040
tctcaagaag atcctttgat cttttctacg ggtctgacg ctcagtggaa cgaaaactca    8100
cgttaaggga ttttggtcat gagattatca aaaggatct tcacctagat cctttaaat    8160
taaaatgaa gttttaaatc aatctaaagt atatatgagt aaacttggtc tgacagttac    8220
caatgcttaa tcagtgaggc acctatctca gcgatctgtc tatttcgttc atccatagtt    8280
gcctgactcc ccgtcgtgta gataactacg atacgggagg gcttaccatc tggccccagt    8340
gctgcaatga taccgcgaga cccacgctca ccggctccag atttatcagc aataaaccag    8400
ccagccggaa gggccgagcg cagaagtggt cctgcaactt tatccgcctc catccagtct    8460
attaattgtt gccgggaagc tagagtaagt agttcgccag ttaatagttt gcgcaacgtt    8520
gttgccattg ctgcaggcat cgtggtgtca cgctcgtcgt ttggtatggc ttcattcagc    8580
tccggttccc aacgatcaag gcgagttaca tgatccccca tgttgtgcaa aaaagcggtt    8640
agctccttcg gtcctccgat cgttgtcaga agtaagttgg ccgcagtgtt atcactcatg    8700
gttatggcag cactgcataa ttctcttact gtcatgccat ccgtaagatg cttttctgtg    8760
actggtgagt actcaaccaa gtcattctga aatagtgta gcggcgacc gagttgctct    8820
tgcccggcgt caacacggga taataccgcg ccacatagca gaactttaaa agtgctcatc    8880
attggaaaac gttcttcggg gcgaaaactc tcaaggatct taccgctgtt gagatccagt    8940
tcgatgtaac ccactcgtgc acccaactga tcttcagcat cttttacttt caccagcgtt    9000
tctgggtgag caaaaacagg aaggcaaaat gccgcaaaaa agggaataag ggcgacacgg    9060
aaatgttgaa tactcatact cttccttttt caatattatt gaagcattta tcagggttat    9120
tgtctcatga gcggatacat atttgaatgt atttagaaaa ataaacaaat aggggttccg    9180
cgcacatttc cccgaaaagt gccacctgac gtctaagaaa ccattattat catgacatta    9240
acctataaaa ataggcgtat cacgaggccc tttcgtcttc aagaattccg atccagacat    9300
gataagatac attgatgagt ttggacaaac cacaactaga atgcagtgaa aaaaatgctt    9360
tatttgtgaa atttgtgatg ctattgcttt atttgtaacc attagaagct gcaataaaca    9420
agttaacaac aacaattgca ttcattttat gtttcaggtt caggggggagg tgtgggaggt    9480
tttttaaagc aagtaaaacc tctacaaatg tggtatggct gattatgatc taaagccagc    9540
aaaagtccca tggtcttata aaatgcata gctttcggag gggagcagag aacttgaaag    9600
catcttcctg ttagtctttc ttctcgtaga ccttaaattc atacttgatt cctttttcct    9660
cctgacctc agagaggacg cctgggtatt ctggagaag tttatatttc cccaaatcaa    9720
tttctgggaa aaacgtgtca ctttcaaatt cctgcatgat ccttgtcaca aagagtctga    9780
ggtggcctgg ttgattcatg gcttcctggt aaacagaact gcctccgact atccaaacca    9840
tgtctacttt acttgccaat tccggttgtt caataagtct taaggcatca tccaaacttt    9900
```

-continued

```
tggcaagaaa atgagctcct cgtggtggtt ctttgagttc tctactgaga actatattaa    9960
ttctgtcctt taaaggtcga ttcttctcag gaatggagaa ccaggttttc ctacccataa   10020
tcaccagatt ctgtttacct tccactgaag aggttgtggt cattctttgg aagtacttga   10080
actcgttcct gagcggaggc cagggtcggt ctccgttctt gccaatcccc atattttggg   10140
acacggcgac gatgcagttc aatggtcgaa ccatgagggc accaagctag cttttttgcaa  10200 aagcctaggc ctccaaaaaa gcctcctcac tacttctgga atagctcaga ggccgaggcg   10260
gcctcggcct ctgcataaat aaaaaaaatt agtcagccat ggggcggaga atgggcggaa   10320 ctggcggag ttaggggcgg gatgggcgga gttaggggcg ggactatggt tgctgactaa    10380
ttgagatgca tgctttgcat acttctgcct gctggggagc ctggggactt tccacacctg   10440
gttgctgact aattgagatg catgctttgc atacttctgc ctgctgggga gcctggggac   10500
tttccacacc ctaactgaca cacattccac a                                   10531
```

```
<210> SEQ ID NO 5
<211> LENGTH: 220
<212> TYPE: PRT
<213> ORGANISM: Artificial Sequence
<220> FEATURE:
<223> OTHER INFORMATION: Humanized Immunoglobulin Light chain

<400> SEQUENCE: 5

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 6
<211> LENGTH: 575
<212> TYPE: PRT
```

<213> ORGANISM: Artificial Sequence
<220> FEATURE:
<223> OTHER INFORMATION: Humanized Immunoglobulin Heavy Chain-IL-2

<400> SEQUENCE: 6

```
Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
                85                  90                  95

Val Ser Gly Met Glu Tyr Trp Gly Gln Gly Thr Ser Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
```

-continued

```
385                 390                 395                 400
Phe Leu Tyr Ser Lys Leu Thr Val Asp Lys Ser Arg Trp Gln Gln Gly
            405                 410                 415
Asn Val Phe Ser Cys Ser Val Met His Glu Ala Leu His Asn His Tyr
            420                 425                 430
Thr Gln Lys Ser Leu Ser Leu Ser Pro Gly Ala Pro Thr Ser Ser Ser
            435                 440                 445
Thr Lys Lys Thr Gln Leu Gln Leu Glu His Leu Leu Leu Asp Leu Gln
    450                 455                 460
Met Ile Leu Asn Gly Ile Asn Asn Tyr Lys Asn Pro Lys Leu Thr Arg
465                 470                 475                 480
Met Leu Thr Phe Lys Phe Tyr Met Pro Lys Lys Ala Thr Glu Leu Lys
            485                 490                 495
His Leu Gln Cys Leu Glu Glu Glu Leu Lys Pro Leu Glu Glu Val Leu
            500                 505                 510
Asn Leu Ala Gln Ser Lys Asn Phe His Leu Arg Pro Arg Asp Leu Ile
            515                 520                 525
Ser Asn Ile Asn Val Ile Val Leu Glu Leu Lys Gly Ser Glu Thr Thr
    530                 535                 540
Phe Met Cys Glu Tyr Ala Asp Glu Thr Ala Thr Ile Val Glu Phe Leu
545                 550                 555                 560
Asn Arg Trp Ile Thr Phe Cys Gln Ser Ile Ile Ser Thr Leu Thr
            565                 570                 575
```

IMMUNOCYTOKINE SEQUENCES AND USES THEREOF

CROSS REFERENCE TO RELATED APPLICATION

This incorporates by reference, and claims priority to and the benefit of, U.S. provisional patent application 60/433,945, which was filed on Dec. 17, 2002.

FIELD OF THE INVENTION

This invention relates generally to modified antibodies. More particularly, the invention relates to modified antibodies with reduced immunogenicity that specifically bind the human cell surface glycosphingolipid GD2, and their use as therapeutic agents.

BACKGROUND OF THE INVENTION

There has been significant progress in the development of antibody-based therapies over the years. For example, investigators have identified not only a variety of cancer-specific markers but also a variety of antibodies that specifically bind to those markers. Antibodies can be used to deliver certain molecules, for example, a toxin or an immune stimulatory moiety, for example, a cytokine, to a cancer cell expressing the marker so as to selectively kill the cancer cell.

The 14.18 antibody is a mouse-derived monoclonal antibody directed against the cell surface glycosphingolipid GD2. GD2 is a disialoganglioside that is normally only expressed at a significant level on the outer surface membranes of neuronal cells, where its exposure to the immune system is limited by the blood brain barrier.

Many tumor cells, in contrast, have abnormal levels of glycosphingolipid cell surface expression. For example, GD2 is expressed on the surfaces of a wide range of tumor cells including neuroblastomas, medulloblastomas, astrocytomas, melanomas, small-cell lung cancer, osteosarcomas and other soft tissue sarcomas. Thus, GD2 is a convenient tumor-specific marker for targeting immune-stimulatory protein domains to tumor cells for the purpose of raising an effective immune response against the tumor cells to destroy them. While the 14.18 mouse antibody (m14.18 antibody) may assist the targeting of these protein domains to tumor cells, its mouse-derived amino acid sequences can impair the desired therapeutic effect.

When administered to a patient, antibodies can have an associated immunogenicity in the host mammal. This is more likely to occur when the antibodies are not autologous. Consequently, the effectiveness of antibody-based therapies often is limited by an immunogenic response directed against the therapeutic antibody. This immunogenic response typically is increased when the antibody is derived in whole or in part from a mammal different than the host mammal, e.g., when the antibody is derived from a mouse and the recipient is a human.

For clinical use in humans, it may be helpful to modify mouse-derived antibodies to more closely resemble human antibodies, so as to reduce or minimize the immunogenicity of the mouse-derived antibody. The immunogenicity of the mouse-derived antibody can be reduced by the creation of a chimeric antibody in which the constant regions of a human antibody are fused to mouse variable domains. However, the remaining mouse variable domains are generally still immunogenic in humans, and can thus impair the efficacy of an antibody-based therapy.

Some approaches to reducing immunogenicity, such as "veneering" and "humanization" involve the introduction of many amino acid substitutions and may disrupt the binding of an antibody to an antigen. The m14.18 antibody binds to GD2 with moderate affinity. Therefore, mutations that significantly lower the affinity of m14.18 for GD2 are expected to make it less effective for therapeutic purposes in humans. Accordingly, there is a need in the art for therapeutic antibodies that can effectively target GD2 and have reduced immunogenicity when administered to a human.

SUMMARY OF THE INVENTION

Generally, the present invention provides a modified form of the m14.18 antibody that is less immunogenic in humans, but still maintains the binding affinity of m14.18 for human GD2.

More particularly, the invention provides a humanized form of the m14.18 antibody (hu14.18 antibody) in which several mouse-specific amino acids in one or more of the framework regions have been substituted with different amino acids to reduce their immunogenicity in humans. The invention also provides fusions of the hu14.18 antibody to one or more non-immunoglobulin moieties for enhancing the effects of targeted immune therapy.

In one aspect, the present invention provides an antibody variable region including the amino acid sequence set forth in SEQ ID NO: 1, which defines an immunoglobulin light chain variable region ($V_L$ region). In another aspect, the invention relates to an antibody variable region including the amino acid sequence set forth in SEQ ID NO: 2, which defines an immunoglobulin heavy chain variable region ($V_H$ region). In one embodiment, the invention provides an antibody variable region in which the amino acid sequence of SEQ ID NO: 1 is linked to the amino acid sequence set forth in SEQ ID NO: 2. The amino acid sequences can be linked, such as by a disulfide bond or a peptide bond.

In another aspect, the invention relates to an antibody variable region that specifically binds to GD2 and includes at least amino acids 1–23 of SEQ ID NO: 1, amino acids 1–25 of SEQ ID NO: 2, or amino acids 67–98 of SEQ ID NO: 2. These sequences define framework regions in the immunoglobulin variable regions of the hu14.18 antibody. Framework regions are described in greater detail below.

One aspect of the invention relates to a method for targeting a cell with GD2 on its surface and includes administering an antibody variable region of the present invention to a patient. In one embodiment, the targeted cell is a tumor cell. Further aspects of the invention include a nucleic acid encoding the antibody variable region or a cell that includes this nucleic acid, either of which can be administered to a patient or used for in vitro protein production.

The invention also provides a polypeptide that includes an antibody variable region of the invention and an Fc portion comprising at least a CH2 domain, nucleic acids encoding the polypeptide, cells including the nucleic acids, and methods for targeting a cell with GD2 on its surface by administering the polypeptide, nucleic acid, or cell to a patient. In some embodiments of the invention, the Fc portion is derived from IgG1.

The antibody variable region can be linked, with or without an intervening Fc portion, to a non-immunoglobulin moiety. Specifically, the non-immunoglobulin moiety can be a cytokine, such as an interleukin, a hematopoietic factor, a lymphokine, an interferon, or a chemokine. The interleukin can be, for example, interleukin-2 or interleukin-12. The hematopoietic factor and lymphokine can be, for example, granulocyte-macrophage colony stimulating factor (GM-CSF) and a lymphotoxin, respectively. The interferon can be, for example, interferon-α, interferon-β, or interferon-γ. In some embodiments of the invention, the fusion protein includes a second non-immunologlobulin moiety, such as a second cytokine. In a particular embodiment, the fusion protein includes the antibody variable region, IL-2, and IL-12.

It is to be understood that the features of the various embodiments described herein are not mutually exclusive and can exist in various combinations and permutations.

DESCRIPTION OF THE DRAWINGS

FIGS. 2A–G show the nucleotide sequence of a vector for expression of an immunoglobulin light chain and an immunoglobulin heavy chain-IL-2 fusion protein in accordance with the invention. The nucleotide sequence is presented in 5' to 3' direction from left to right and top to bottom, spanning FIGS. 2A–2G, and is SEQ ID NO: 4.

FIG. 3A shows the amino acid sequence of an immunoglobulin light chain in accordance with the invention.

FIG. 3B shows the amino acid sequence of an immunoglobulin heavy chain in accordance with the invention.

DETAILED DESCRIPTION OF THE INVENTION

The present invention provides a modified form of the m14.18 antibody that is less immunogenic in humans, but is still able to specifically bind human GD2. The reduced immunogenicity is provided by one or more altered amino acid sequences in the immunoglobulin variable domains. The antibody is useful for treating GD2-positive tumors, particularly when fused to a cytokine or other immune modulator.

As used herein, the terms "antibody" and "immunoglobulin" are understood to mean (i) an intact antibody (for example, a monoclonal antibody or polyclonal antibody), (ii) antigen binding portions thereof, including, for example, an Fab fragment, an Fab' fragment, an (Fab')$_2$ fragment, an Fv fragment, a single chain antibody binding site, an sFv, (iii) bi-specific antibodies and antigen binding portions thereof, and (iv) multi-specific antibodies and antigen binding portions thereof.

As used herein, the terms "bind specifically," "specifically bind" and "specific binding" are understood to mean that the antibody has a binding affinity for a particular antigen of at least about $10^6$ M$^{-1}$, more preferably, at least about $10^7$ M$^{-1}$, more preferably at least about $10^8$ M$^{-1}$, and most preferably at least about $10^{10}$ M$^{-1}$.

As used herein, the terms "Framework Regions" and "FRs" are understood to mean the regions of an immunoglobulin variable region adjacent to the Complementarity-Determining Regions (CDRs). CDRs are the portions of an immunoglobulin variable region that interact primarily with an antigen. As shown in FIG. 1, the $V_H$ and $V_L$ regions both contain four FRs and are located within the boxed portions of the amino acid sequences.

Figure 1A:
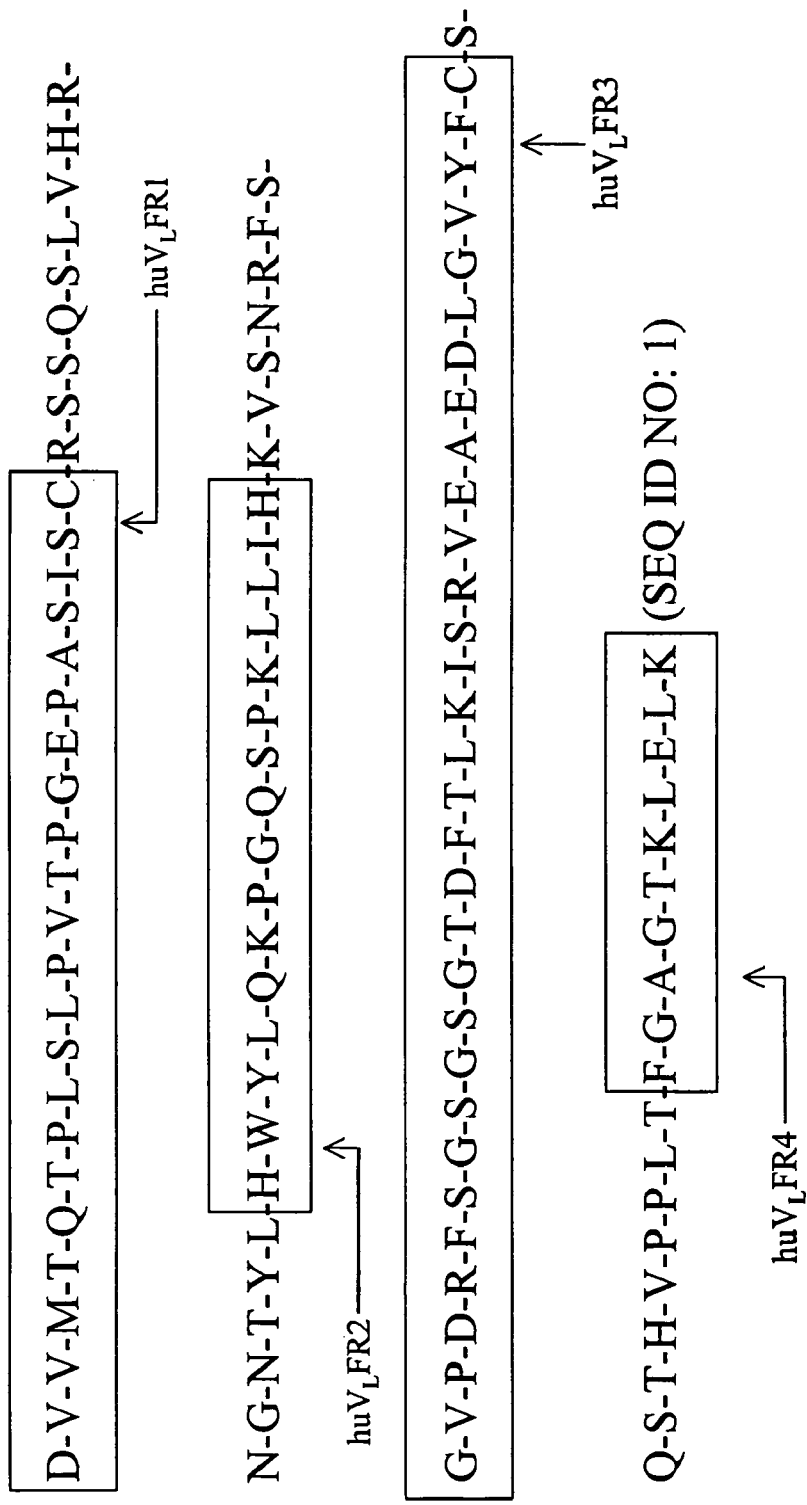
FIG. 1A shows the amino acid sequence of an immunoglobulin light chain variable region in accordance with the invention.
Figure 1B:
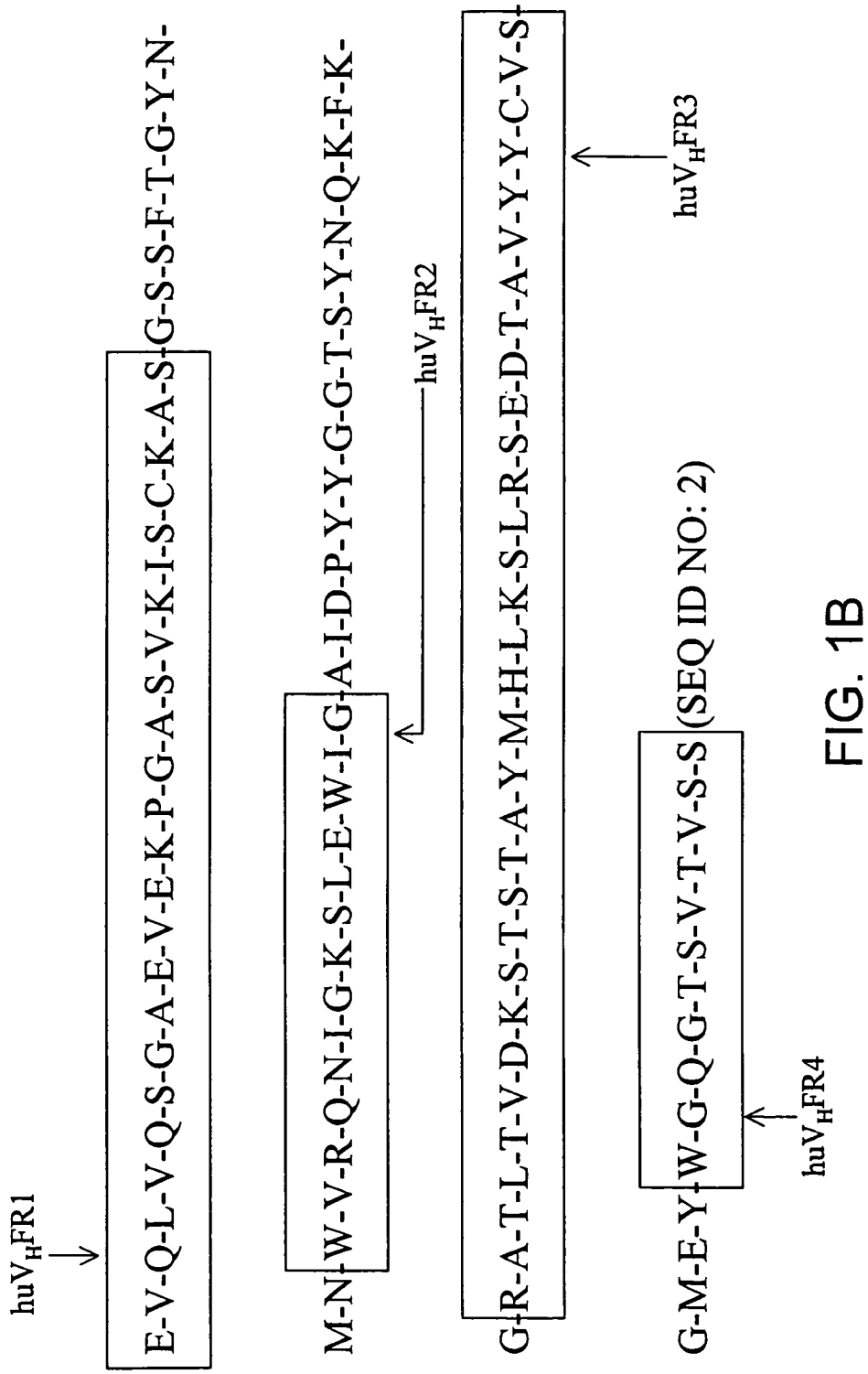
FIG. 1B shows the amino acid sequence of an immunoglobulin heavy chain variable region in accordance with the invention.

In particular, with reference to the amino acid sequence shown in FIG. 1A (SEQ ID NO: 1), the light chain FRs are defined by the amino acid sequences from Asp1 to Cys23 (huV$_L$FR1), from His39 to His54 (huV$_L$FR2), from Gly62 to Cys93 (huV$_L$FR3), and from Phe104 to Lys113 (huV$_L$FR4). With reference to the amino acid sequence shown in FIG. 1B (SEQ ID NO: 2), the heavy chain FRs are defined by the amino acid sequences from Glu1 to Ser25 (huV$_H$FR1), from Trp36 to Gly49 (huV$_H$FR2), from Arg67 to Ser98 (huV$_H$FR3), and from Trp103 to Ser113 (huV$_H$FR4).

Protein Sequences of the Invention

The present invention features antibodies that bind, preferably specifically, to the human cell surface glycosphingolipid GD2 and have modified regions derived from the m14.18 antibody. The $V_H$ or $V_L$ amino acid sequences (or both) are modified or humanized to reduce their immunogenicity when administered to a human. In accordance with the invention, the m14.18 antibody can be humanized, for example, by using deimmunization methods in which potential T cell epitopes are eliminated or weakened by introduction of mutations that reduce binding of a peptide epitope to an MHC Class II molecule (see, for example, WO98/52976 and WO00/34317). Alternatively, non-human T cell epitopes are mutated so that they correspond to human self epitopes that are present in human antibodies (see, for example, U.S. Pat. No. 5,712,120). The present invention provides GD2 antibodies having $V_L$ and $V_H$ regions that include at least one humanized FR sequence, thereby reducing immunogenicity when administered to a human.

I. Heavy and Light Chains Variable Regions

As mentioned above, the hu14.18 includes humanized variable regions derived from the m14.18 antibody that maintain specific binding of human GD2 antigen. In some embodiments of the invention, the $V_L$ region of the hu14.18 antibody includes the following polypeptide:

```
D-V-V-M-T-Q-T-P-L-S-L-P-V-T-P-G-E-P-A-S-I-S-C-R-S-S-Q-S-L-V-H-R-N-G-N-T-  (SEQ ID NO: 1)

Y-L-H-W-Y-L-Q-K-P-G-Q-S-P-K-L-L-I-H-K-V-S-N-R-F-S-G-V-P-D-R-F-S-G-S-G-S-

G-T-D-F-T-L-K-I-S-R-V-E-A-E-D-L-G-V-Y-F-C-S-Q-S-T-H-V-P-P-L-T-F-G-A-G-T-

K-L-E-L-K.
```

In particular embodiments, the hu14.18 antibody includes a light chain FR1 that is defined by residues 1 to 23 of SEQ ID NO: 1, namely, D-V-V-M-T-Q-T-P-L-S-L-P-V-T-P-G-E-P-A-S-I-S-C (huV$_L$FR1).

In other embodiments of the invention, the V$_H$ region of the hu14.18 antibody includes the following polypeptide:

```
E-V-Q-L-V-Q-S-G-A-E-V-E-K-P-G-A-S-V-K-I-S-C-K-A-S-G-S-S-F-T-G-Y-N-M-N-    (SEQ ID NO: 2)
W-V-R-Q-N-I-G-K-S-L-E-W-I-G-A-I-D-P-Y-Y-G-G-T-S-Y-N-Q-K-F-K-G-R-A-T-L-T-
V-D-K-S-T-S-T-A-Y-M-H-L-K-S-L-R-S-E-D-T-A-V-Y-Y-C-V-S-G-M-E-Y-W-G-Q-G-
T-S-V-T-V-S-S.
```

In particular embodiments, the hu14.18 antibody includes a heavy chain FR1 that is defined by residues 1 to 25 of SEQ ID NO: 2, namely E-V-Q-L-V-Q-S-G-A-E-V-E-K-P-G-A-S-V-K-I-S-C-K-A-S (huV$_H$FR1).

In further embodiments of the invention, the hu14.18 antibody includes a heavy chain FR3 that is represented by residues 67 to 98 of SEQ ID NO: 2, namely R-A-T-L-T-V-D-K-S-T-S-T-A-Y-M-H-L-K-S-L-R-S-E-D-T-A-V-Y-Y-C-V-S (huV$_H$FR3).

Various combinations of the foregoing embodiments are also within the scope of the present invention. For example, the hu14.18 antibody may include the V$_L$ sequence set forth in SEQ ID NO: 1 and the V$_H$ sequence set forth in SEQ ID NO: 2. The V$_L$ and V$_H$ regions can be linked by a disulfide bond or a peptide bond, depending on how their nucleic acid sequences are constructed. In general, V regions are linked by a disulfide bond when their sequences are encoded on separate DNA constructs. In contrast, the V regions are typically linked by a peptide bond when their sequences are encoded on a single-chain DNA construct.

The present invention also contemplates an antibody that specifically binds GD2 and includes at least a portion of the humanized V regions. For example, the hu14.18 antibody can include a V$_L$ region as defined by SEQ ID NO:1 and a V$_H$ region having at least one humanized FR, such as huV$_H$FR1 or huV$_H$FR2. Alternatively, the antibody of the present invention can include a V$_H$ region as defined by SEQ ID NO: 2 and a V$_L$ region having at least one humanized FR, such as huV$_L$FR1. The hu14.18 antibody can also include a V$_H$ region having at least one humanized FR and/or a V$_L$ region having at least one humanized FR.

In certain embodiments of the invention, the light chain variable region and the heavy chain variable region can be coupled, respectively, to a light chain constant region and a heavy chain constant region of an immunoglobulin. The immunoglobulin light chains have constant regions that are designated as either kappa or lambda chains. In a particular embodiment of the invention, the light chain constant region is a kappa chain. The heavy chain constant regions, and various modification and combinations thereof are discussed below in detail.

II. Fc Portion

The antibody variable domains of the present invention are optionally fused to an Fc portion. As used herein, the Fc portion encompasses domains derived from the heavy chain constant region of an immunoglobulin, preferably a human immunoglobulin, including a fragment, analog, variant, mutant or derivative of the constant region. The constant region of an immunoglobulin heavy chain is defined as a naturally-occurring or synthetically produced polypeptide homologous to at least a portion of the C-terminal region of the heavy chain, including the CH1, hinge, CH2, CH3, and, for some heavy chain classes, CH4 domains. The "hinge" region joins the CH1 domain to the CH2–CH3 region of an Fc portion. The constant region of the heavy chains of all mammalian immunoglobulins exhibit extensive amino acid sequence similarity. DNA sequences for these immunoglobulin regions are well known in the art. (See, e.g., Gillies et al. (1989) *J. Immunol. Meth.* 125:191).

In the present invention, the Fc portion typically includes at least a CH2 domain. For example, the Fc portion can include the entire immunoglobulin heavy chain constant region (CH1-hinge-CH2–CH3). Alternatively, the Fc portion can include all or a portion of the hinge region, the CH2 domain and the CH3 domain.

The constant region of an immunoglobulin is responsible for many important antibody effector functions, including Fc receptor (FcR) binding and complement fixation. There are five major classes of the heavy chain constant region, classified as IgA, IgG, IgD, IgE, and IgM, each with characteristic effector functions designated by isotype.

IgG, for example, is separated into four γ isotypes: γ1, γ2, γ3, and γ4, also known as IgG1, IgG2, IgG3, and IgG4, respectively. IgG molecules can interact with multiple classes of cellular receptors including three classes of Fcγ receptors (FcγR) specific for the IgG class of antibody, namely FcγRI, FcγRII, and FcγRIII. The sequences important for the binding of IgG to the FcγR receptors have been reported to be in the CH2 and CH3 domains.

The serum half-life of an antibody is influenced by the ability of that antibody to bind to an Fc receptor (FcR). Similarly, the serum half-life of immunoglobulin fusion proteins is also influenced by the inability to bind to such receptors (Gillies et al., *Cancer Research* (1999) 59:2159–66). The CH2 and CH3 domains of IgG2 and IgG4 have undetectable or reduced binding affinity to Fc receptors compared to those of IgG1. Accordingly, the serum half-life of the featured antibody can be increased by using the CH2 and/or CH3 domain from IgG2 or IgG4 isotypes. Alternatively, the antibody can include a CH2 and/or CH3 domain from IgG1 or IgG3 with modification in one or more amino acids in these domains to reduce the binding affinity for Fc receptors (see, e.g., U.S. patent application Ser. No. 09/256, 156, published as U.S. patent application publication 2003-0105294-A1).

The hinge region of the Fc portion normally adjoins the C-terminus of the CH1 domain of the heavy chain constant region. When included in the proteins of the present invention, the hinge is homologous to a naturally-occurring immunoglobulin region and typically includes cysteine residues linking two heavy chains via disulfide bonds as in natural immunoglobulins. Representative sequences of hinge regions for human and mouse immunoglobulin can be found in ANTIBODY ENGINEERING, a PRACTICAL GUIDE, (Borrebaeck, ed., W. H. Freeman and Co., 1992).

Suitable hinge regions for the present invention can be derived from IgG1, IgG2, IgG3, IgG4, and other immunoglobulin isotypes. The IgG1 isotype has two disulfide bonds in the hinge region permitting efficient and consistent disulfide bonding formation. Therefore, a preferred hinge region of the present invention is derived from IgG1. Optionally, the first, most N-terminal cysteine of an IgG1 hinge is mutated to enhance the expression and assembly of antibodies or antibody fusion proteins of the invention (see, e.g., U.S. patent application Ser. No. 10/093,958, published as U.S. patent application publication 2003-0044423-A1).

In contrast to IgG1, the hinge region of IgG4 is known to form interchain disulfide bonds inefficiently (Angal et al., (1993), *Mol. Immunol.* 30:105–8). Also, the IgG2 hinge region has four disulfide bonds that tend to promote oligomerization and possibly incorrect disulfide bonding during secretion in recombinant systems. One suitable hinge region for the present invention can be derived from the IgG4 hinge region, preferentially containing a mutation that enhances correct formation of disulfide bonds between heavy chain-derived moieties (Angal et al., (1993), *Mol. Immunol.* 30(1): 105–8). Another preferred hinge region is derived from an IgG2 hinge in which the first two cysteines are each mutated to another amino acid, such as, in order of general preference, serine, alanine, threonine, proline, glutamic acid, glutamine, lysine, histidine, arginine, asparagine, aspartic acid, glycine, methionine, valine, isoleucine, leucine, tyrosine, phenylalanine, tryptophan or selenocysteine (see, e.g., U.S. patent application publication 2003-0044423-A1).

An Fc portion fused to an antibody variable region of the invention can contain CH2 and/or CH3 domains and a hinge region that are derived from different antibody isotypes. For example, the Fc portion can contain CH2 and/or CH3 domains of IgG2 or IgG4 and a hinge region of IgG1. Assembly of such hybrid Fc portions has been described in U.S. patent application publication 2003-0044423-A1.

When fused to an antibody variable region of the invention, the Fc portion preferably contains one or more amino acid modifications that generally extend the serum half-life of an Fc fusion protein. Such amino acid modifications include mutations substantially decreasing or eliminating Fc receptor binding or complement fixing activity. For example, one type of such mutation removes the glycosylation site of the Fc portion of an immunoglobulin heavy chain. In IgG1, the glycosylation site is Asn297 (see, for example, U.S. patent application Ser. No. 10/310,719, published as U.S. patent application publication 2003-0166163-A1).

III. Fusion Junction Region

The antibody variable regions of the present invention can optionally be linked or fused to a non-immunoglobulin moiety directly or indirectly, such as through a linker peptide (e.g., (Gly$_4$-Ser)$_3$ (SEQ ID NO: 3)). The immunogenicity of the disclosed fusion proteins can be reduced by impairing the ability of the fusion junction or junctional epitope to interact with a T-cell receptor, as described in U.S. patent application publication 2003-0166877-A1. Even in a fusion between two human proteins, e.g., human Fc and human IL-2, the region surrounding the fusion junction or junctional epitope includes a peptide sequence that is not normally present in the human body and, thus, that can be immunogenic. The immunogenicity of the junctional epitope can be reduced, for example, by introducing one or more glycosylation sites near the fusion junction, or by identifying a candidate T-cell epitope spanning the junction as described in U.S. patent application publication 2003-0166877-A1 and changing an amino acid near the junction to reduce the ability of the candidate T-cell epitope to interact with a T-cell receptor.

The serum half-life of the protein can also be increased by introducing mutations into the fusion junction region. For example, in a protein including a CH3 domain fused to a non-immunoglobulin moiety, the C-terminal lysine of the CH3 domain can be changed to another amino acid, such as alanine, which can provide a substantial increase in serum half-life of the resulting fusion protein.

In certain embodiments, proteolytic cleavage of the fusion junction is desirable. Accordingly, the intergenic region can include a nucleotide sequence encoding a proteolytic cleavage site. This site, interposed between the immunoglobulin and the cytokine, can be designed to provide for proteolytic release of the cytokine at the target site. For example, it is well known that plasmin and trypsin cleave after lysine and arginine residues at sites that are accessible to the proteases. Other site-specific endoproteases and the amino acid sequences they recognize are well-known.

IV. Treatment of Human Disease with hu14.18 Antibody Fusion Proteins

The antibody variable regions of the invention can be attached to a diagnostic and/or a therapeutic agent. The agent can be fused to the antibody to produce a fusion protein. Alternatively, the agent can be chemically coupled to the antibody to produce an immuno-conjugate. The agent can be, for example, a toxin, radiolabel, imaging agent, immunostimulatory moiety or the like.

The antibody variable region of the invention can be attached to a cytokine. Preferred cytokines include interleukins such as interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), granulocyte colony stimulating factor (G-CSF) and erythropoeitin, tumor necrosis factors (TNF) such as TNFα, lymphokines such as lymphotoxin, regulators of metabolic processes such as leptin, interferons such as interferon α, interferon β, and interferon γ, and chemokines. Preferably, the antibody-cytokine fusion protein or immunoconjugate displays cytokine biological activity. In one embodiment, the antibody variable domain is fused to IL-2. Preferably, several amino acids within the IL-2 moiety are mutated to reduce toxicity, as described in U.S. patent application publication 2003-0166163-A1.

For example, FIGS. 3A and 3B show the amino acid sequences of a particular embodiment of an antibody fusion protein in accordance with the invention. Specifically, FIG. 3A shows the peptide sequence of a humanized immunoglobulin light chain that includes a variable and constant region. FIG. 3B shows the peptide sequence of a humanized immunoglobulin heavy chain linked to IL-2. The polypeptides provide a humanized antibody fusion protein capable of specifically binding to GD2 and stimulating the immune system.

Optionally, the protein complexes can further include a second agent, such as a second cytokine. In one embodiment, a hu14.18 antibody fusion protein includes IL-12 and IL-2. The construction of protein complexes containing an immunoglobulin domain and two, different cytokines is described in detail in U.S. Pat. No. 6,617,135.

Fusion proteins of the present invention are useful in treating human disease, such as cancer. When treating human tumors, it is particularly useful to administer an antibody-IL-2 fusion protein comprising the V regions of the invention by infusion or subcutaneous injection, using doses of 0.1 to 100 milligrams/meter$^2$/patient. In a preferred embodiment, it is particularly useful to administer an antibody-IL-2 fusion protein comprising the V regions of the invention by infusion or subcutaneous injection, using doses of 1 to 10 milligrams/meter$^2$/patient, and more preferably about 3 to 6 milligrams/meter$^2$/patient.

Clinical studies have shown that following administration of hu14.18-IL-2, the fusion protein retains its ability to activate IL-2 responsive cells through the IL-2 receptor and retains its ability to bind to GD2-positive tumor cells and to deliver IL-2 to their surface. Furthermore, administration of hu14.18-IL-2 fusion protein to a cancer patients resulted in stabilization of disease progression in a surprisingly large number of patients (see Example 1).

Pharmaceutical compositions of the invention may be used in the form of solid, semisolid, or liquid dosage forms, such as, for example, pills, capsules, powders, liquids, suspensions, or the like, preferably in unit dosage forms suitable for administration of precise dosages. The compositions include a conventional pharmaceutical carrier or excipient and, in addition, may include other medicinal agents, pharmaceutical agents, carriers, adjuvants, etc. Such excipients may include other proteins, such as, for example, human serum albumin or plasma proteins. Actual methods of preparing such dosage forms are known or will be apparent to those skilled in the art. The composition or formulation to be administered will, in any event, contain a quantity of the active component(s) in an amount effective to achieve the desired effect in the subject being treated.

Administration of the compositions hereof can be via any of the accepted modes of administration for agents that exhibit such activity. These methods include oral, parenteral, or topical administration and otherwise systemic forms. Intravenous injection in a pharmaceutically acceptable carrier is a preferred method of administration (see Example 1).

The amount of active compound administered will, of course, be dependent on the subject being treated, the severity of the affliction, the manner of administration, and the judgment of the prescribing physician.

Nucleic Acids of the Invention

I. hu14.18 Antibody Constructs

The invention also features nucleic acids capable of expressing each of the above types of proteins. These include, for example, nucleic acids encoding the amino acid sequence set forth in SEQ ID NO: 1; the amino acid sequence set forth in SEQ ID NO: 2; a hu14.18 antibody $V_L$ region that includes the huV$_L$FR1 amino acid sequence; a hu14.18 antibody $V_H$ region that includes the huV$_H$FR1 amino acid sequence; a hu14.18 antibody $V_H$ region that includes hUV$_H$FR3 amino acid sequence; and fusion proteins comprising a hu14.18 antibody including at least one of the foregoing humanized FR sequences and one or more therapeutic agents.

The hu14.18 antibodies of this invention can be produced by genetic engineering techniques; i.e., by forming a nucleic acid construct encoding an GD2 specific antibody containing the desired FRs of the present invention. In one embodiment, the gene construct encoding the featured antibody includes, in 5' to 3' orientation, a DNA segment which encodes a heavy chain variable region including at least one humanized FR therein and a DNA segment encoding a heavy chain constant region. In another embodiment, another DNA segment encoding a cytokine is fused to the 3' end of the DNA segment encoding the heavy chain constant region. In a different embodiment, the gene construct includes, in 5' to 3' orientation, a DNA segment encoding a heavy chain variable region including at least one humanized FR and a DNA segment encoding a cytokine. Alternatively, a nucleic acid of the invention can include, in 5' to 3' orientation, a DNA segment encoding a light chain variable region including at least one humanized FR therein and a DNA segment encoding a cytokine. In some embodiments, a nucleic acid encoding a cytokine is joined in frame to the 3' end of a gene encoding a constant region (e.g., CH3 exon), either directly or through an intergenic region (e.g., by appropriate linkers, such as by DNA encoding (Gly$_4$ -Ser)$_3$ (SEQ ID NO: 3)).

II. Expression of hu14.18 Antibody Constructs

Nucleic acid encoding proteins of the present invention can be assembled or inserted into one or more expression vectors for introduction into an appropriate recipient cell where it is expressed. The introduction of nucleic acids into expression vectors can be accomplished by standard molecular biology techniques. Preferred expression vectors include those from which the encoded protein can be expressed in either bacteria or mammalian cells.

In accordance with the invention, a heavy chain of an antibody variable region is preferably co-expressed in the same cell with a corresponding light chain. For fusion proteins that comprise multiple polypeptide chains, more than one expression vector can be used. Co-transfection methods using, for example, two expression vectors, frequently result in both vectors being delivered to a target cell. Alternatively, it is sometimes useful to use a single vector encoding a plurality of polypeptides for co-expression in the same cell.

For example, FIGS. 2A–G show the nucleic acid sequence of a single vector encoding both the heavy and light chains of an immunoglobulin in accordance with the invention. The vector also includes a nucleic acid encoding IL-2 fused to the 3' end of the immunoglobulin heavy chain. Thus, when introduced into a cell, this vector alone can provide a humanized antibody-IL-2 fusion protein that specifically binds GD2 and stimulates immune function.

Furthermore, it can be convenient to express the proteins of the present invention as single-chain molecules. For example, an antibody variable region can be expressed as a single chain antibody or sFv optionally fused to a non-immunoglobulin protein. In another embodiment, a heavy chain (with or without a fused cytokine) is combined with a light (or heavy) chain counterpart (with or without a fused cytokine) to form monovalent and divalent immunoconjugates.

Recipient cell lines are preferably lymphoid cells, such as a myeloma (or hybridoma). Myelomas can synthesize, assemble, and secrete immunoglobulins encoded by transfected genes and can glycosylate proteins. A particularly preferred recipient cell is the Sp2/0 myeloma, which normally does not produce endogenous immunoglobulin. When transfected, the cell will produce only immunoglobulins encoded by the transfected gene constructs. Transfected myelomas can be grown in culture or in the peritonea of mice where secreted immunoconjugates can be recovered from ascites fluid. Other lymphoid cells such as B lymphocytes can also be used as recipient cells.

There are several methods for transfecting lymphoid cells with vectors containing the nucleic acid constructs encoding the chimeric Ig chain. A preferred way of introducing a vector into lymphoid cells is by spheroblast fusion. (see, e.g., Gillies et al. (1989) *Biotechnol.* 7:798–804). Alternative methods include electroporation or calcium phosphate precipitation. Other useful methods of producing the immunoconjugates include the preparation of an RNA sequence encoding the construct and its translation in an appropriate in vivo or in vitro system. Once expressed, the proteins of the invention can be harvested by standard protein purification procedures (see, e.g., U.S. Pat. No. 5,650,150).

III. Treatment of Cancer by Gene Therapy

The nucleic acids of the invention can be used as gene therapy agents for treatment of cancer and other diseases in which it is desirable to target the immune system to a specific cell type. For example, cells can be withdrawn from a human or animal, and one or more nucleic acids encoding an antibody of the present invention can be transfected into the cells. The cells are then reintroduced into the human or animal. The transfected cells can be normal or cancer cells. Alternatively, a nucleic acid can be introduced into cells in situ. The human or animal then mounts an immune response to the cancer cells, which can cure or lessen the severity of the cancer. An antibody variable region of the invention, coupled to appropriate regulatory elements to promote expression in mammalian cells, can be transfected into the cells by any of a variety of techniques, including via calcium phosphate, a "gene gun", adenovirus vectors, cationic liposomes, retroviral vectors, or any other efficient transfection method.

In a particular embodiment of the invention, a hu14.18 antibody is used to selectively deliver a cytokine to a target cell in vivo so that the cytokine can exert a localized biological effect such as a local inflammatory response, stimulation of T cell growth and activation, or ADCC activity. A therapeutically effective amount of the antibody is administered into the circulatory system of a subject harboring the target cell.

The invention is illustrated further by the non-limiting examples.

EXAMPLES

Example 1

Purification and Formulation of hu14.18-IL2

In one study, hu14.18-IL2 was expressed from NS/0 cells, tissue culture supernatant was harvested, and the hu14.18-IL2 protein was purified using, in sequence, Abx Mixed Resin column chromatography, recombinant Protein A chromatography, and Q Sepharose column chromatography, followed by Pellicon 2 tangential flow diafiltration for buffer exchange into formulation buffer. Details of these purification steps are described below. Virus inactivation and removal steps were interdigitated into these steps as described below. The virus inactivation and removal steps were not necessary for purification per se, but were used to satisfy regulatory considerations.

Two liters of NS/0 tissue culture supernatant containing hu14.18-IL2 was pH-adjusted to 5.9 with 1M acetic acid and was applied to an Abx column (J. T. Baker); washed with 10 mM MES, 100 mM sodium acetate pH 6.2; and eluted with 500 mM sodium acetate pH 7. This material was loaded onto a recombinant Protein A column (Pharmacia); washed with 100 mM sodium phosphate, 150 mM NaCl pH 7; washed with 100 mM sodium phosphate, 150 mM NaCl pH 6; washed with 10 mM sodium phosphate pH 7; and eluted with 100 mM sodium phosphate, 150 mM NaCl pH 3.5. The pH of the eluted material was 4.2. To promote virus inactivation, this pH was reduced to 3.8 and the preparation was incubated for 30 minutes, after which the pH was neutralized to 7 with 1M NaOH. To remove nucleic acid, this material was loaded onto a Q sepharose column (Pharmacia) and washed with 100 mM sodium phosphate, 150 mM NaCl pH 7. Nucleic acid bound to the column, while the protein was found in the flow through and washes, which were repeated until the A280 returned to baseline. Pellicon 2 diafiltration (Millipore) was performed according to the manufacturer's instructions, so that the final hu14.18-IL2 material was placed in the following formulation.

| | |
|---|---|
| 1. Mannitol | 4% |
| 2. Arginine Hydrochloride USP/NF | 100 mM |
| 3. Citric Acid USP-FCC | 5 mM |
| 4. Polysorbate 80 | 0.01% (w.v) |

The pH of the formulation buffer was adjusted to 7 with 1 M NaOH.

As a final step, the preparation was filtered through a Viresolve 180 membrane (Millipore), which has a molecular weight cutoff of 180,000 Daltons. This had the effect of 'polishing' the material so that as a result, aggregated dimers and higher-order oligomers were removed.

Example 2

Anti-Tumor Activity of the hu14.18-IL-2 Fusion Protein Observed in Phase I Clinical Trials To evaluate the safety and efficacy of hu14.18-IL-2, a Phase I clinical trial was performed. Eligible patients had histologically confirmed melanoma that was considered surgically and medically incurable. These patients could have either measurable or evaluable metastatic disease, or they could have no evidence of disease following surgical resection of either distant metastases or regionally recurrent disease. Patients with multiple (two or more) local or regional recurrences were included only if they had prior evidence of lymph node involvement and if each recurrence was separated in time by at least 2 months. All patients needed to have adequate bone marrow function (defined by total white blood cells (WBC ) >3,500/ml, or total granulocytes >2000/ml, platelets >100,000/ml, and hemoglobin >10.0 g/dl), adequate liver function [defined by an aspartate aminotransferase (AST) <3× normal and a total bilirubin <2.0 mg/dl], and adequate renal function (defined by a serum creatinine <2.0 mg/dl or a creatinine clearance of >60 ml/minute). All patients had an electrocorticography (ECOG) performance status of 0 or 1 and a life expectancy of at least 12 weeks. Patients who had previously received chemotherapy, radiation therapy, or other immunosuppressive therapy within 4 weeks prior to study were excluded. Patients could have prior central nervous system (CNS) metastases if treated and stable for at least 4 weeks prior to starting the study. Informed consent was obtained from all patients.

This phase I trial was designed as an open-label, nonrandomized dose escalation study in which groups of 3 to 6 patients received hu14.18-IL-2 at one of the following dose levels: 0.8, 1.6, 3.2, 4.8, 6.0 or 7.5 mg/m$^2$/day. The hu14.18-IL-2 was administered on an inpatient basis as a 4-hour intravenous (IV) infusion over 3 consecutive days during the first week of each course. The hu14.18-IL-2 fusion protein was administered to patients in a formulation comprising 4% Mannitol; Arginine HCl, 100 mM; Citrate, 5 mM; and 0.01% Tween 80, at pH 7. Patients were discharged from the hospital, if stable, approximately 24 hours following the completion of the third infusion. Adverse events and toxicities were graded as per NCI Common Toxicity Criteria (version 2.0) and the University of Wisconsin Comprehensive Cancer Center Toxicity Grading Scale for IL-2 (performance status, weight gain, and temperature). Dose-limiting toxicity (DLT) was defined as the occurrence of grade 3 or 4 toxicity other than grade 3 lymphopenia, hyperbilirubinemia, hypophosphatemia or hyperglycemia. The maximal tolerated dose (MTD) was defined as the dose level at which two of six patients had DLT during course 1. Patients with grade 3 treatment-related toxicities were required to recover to at least grade 1 before they could resume treatment at a 50% dose reduction for course 2. Patients with $\geq 25\%$ disease progression were removed from the study. Patients with stable disease were administered course 2.

The pharmacokinetic properties of hu14.18-IL-2 were evaluated in the patients. When hu14.18-IL-2 levels were evaluated in serial samples from all 33 patients immediately following the first 4-hour infusion (day 1, course 1), the half-life was found to be 3.7 hours (+/−SD of 0.9 h). This is intermediate between the half-lives of its 2 components (approximately 45 minutes for IL-2 and 3 days for the chimeric m14.18 antibody), and comparable to that which was observed for the half-life of chimeric m14.18-IL-2 in mice. Following the clearance of hu14.18-IL-2 from the serum of these patients, neither the IL-2 nor hu14.18 antibody components could be detected. The peak serum and area under the curve (AUC) during course 1 showed a significant dose-dependent increase ($p<0.001$).

Thirty-three patients were treated in this study. Table 1 lists clinical outcomes. Two patients (6%) completed only the first 2 of 3 days for course 1. One of these patients (dose level 3) had a grade 3 hyperbilirubinemia on day 2 of treatment, and the other patient (dose level 6) had grade 3 hypoxia and hypotension requiring treatment to be held. Both of these patients had progression of disease and did not receive a second course of therapy. Nineteen patients (58%) had stable disease following the first course of therapy and received a second course of therapy. Five patients (15% of all patients) required a 50% dose reduction for course 2 secondary to adverse events in course 1. Seventeen patients (52% of all patients) completed course 2. One patient (dose level 4) declined to receive the final infusion during course 2, and one patient (dose level 6) had the final infusion during course 2 held due to hypotension. Eight patients (24% of all patients) had stable disease following the second course of treatment. The results indicate that hu14.18-IL-2 caused stabilization of disease progression in a surprisingly large number of patients.

Eight of the 33 patients maintained stable disease after 2 courses of therapy, and 4 of these 8 patients continue with no evidence of progressive disease (1 with stable disease and 3 with no evidence of disease) for 20–52 months since completing protocol therapy.

Five of the 33 patients entered the study with no measurable disease following surgical resection of recurrences or metastases. Two of these five patients had disease progression, while the remaining 3 patients continued with no evidence of disease (20–52 months). These findings are consistent with the hypothesis that clinical benefit from an immunotherapeutic intervention is most likely in a patient with a low tumor burden. One additional patient had an objective decrease in a lung nodule following two courses of therapy, but the overall disease response was scored as disease progression due to growth in a distant node. The node was resected following hu14.18-IL-2 therapy and the patient remained free from disease progression for over 3 years.

TABLE 1

Clinical Outcomes

| | Number of Patients |
|---|---|
| Patients completing course 1 | 31 |
| Stable disease following course 1 | 19 |
| 50% dose reduction for course 2 | 5 |
| Patients completing course 2 | 17 |
| Stable disease following course 2 | 8 |

Example 3

Immune Stimulation in vivo by hu14.18-IL-2 in a Phase I Clinical Trial

Patients treated with hu14.18-IL-2 were also examined for indications of immune stimulation. A peripheral blood lymphopenia occurred on days 2–4, and this was followed by a rebound lymphocytosis on days 5–22. Both of these changes were dose-dependent ($p<0.01$ and $p<0.05$, respectively). The lymphocyte counts on days 5, 8, 15 and 22 were significantly greater than baseline for course 1. The baseline lymphocyte count for course 2 (day 29 of course 1) was increased over the baseline lymphocyte count for course 1, indicating that effects of the first course of treatment are still present on day 29. In addition, the lymphocyte counts during course 2 on days 5, 8 and 15 are greater than the corresponding values for days 5, 8, and 15 during course 1 for these 12 patients. Lymphocyte cell surface phenotype showed an expansion of CD16+ and CD56+ lymphocytes (natural killer (NK) cell markers) following the first week of hu14.18-IL-2 therapy. This effect was still present on day 29 of course 1 (day 1, course 2). For patients 19–33 (receiving 4.8–7.5 mg/m$^2$/day), lymphocyte cell surface phenotype was determined on days 15 and 22 in addition to days 1 and 8. This analysis demonstrated that the augmentation of CD56 and CD56/CD16 co-expressing cells remained significantly elevated ($p<0.01$) on days 8, 15 and 22.

As a measure of immune activation, C-reactive protein (CRP) levels for patients 13–33 and soluble IL-2 receptor (sIL-2R) levels for the 31 patients completing course 1, were obtained. A significant increase in mean CRP was present on treatment days 3–5 in both course 1 and course 2 compared to baseline for each course. This increase in CRP returned to baseline levels by day 8 of each treatment course. The sIL-2R level was significantly increased over baseline starting 24 hours after the hu14.18-IL-2 infusion during both course 1 and course 2, which persisted through day 8. The increase in sIL-2R was found to be dose dependent ($p=0.014$). sIL-2R values for course 2 were increased compared to corresponding values in course 1 for days 1–5 for patients receiving the same dose in both courses ($p<0.05$).

The LA-N-5 neuroblastoma cell line that expresses GD2 and binds hu14.18-IL-2 was used to evaluate IL-2 activated NK function and antibody dependent cellular cytotoxicity (ADCC) on peripheral blood mononuclear cells (PBMC) from 31 patients completing course 1. There was a significant increase in killing mediated by lymphocytes from day 8 when compared with day 1 for these two assays. The 12 patients that received course 2 at the same dose as in course 1, showed ADCC results that were very similar to those obtained during course 1. The only parameter that was found to be different for course 2 from course 1 was increased killing in the presence of IL-2 on day 1, indicating that augmented killing in this assay remained elevated on day 29 (day 1, course 2).

Because the LA-N-5 target is relatively resistant to fresh NK cells, it is useful for measuring IL-2 augmented killing, and ADCC. However, the weak killing of LA-N-5 mediated by fresh PBMC in medium (without supplemental IL-2 in vitro) was not significantly greater on day 8 than on day 1.

For patients 19–33, standard NK assays were performed on days 1, 8, 15 and 22, using the NK susceptible K562 target cell line. A significant increase in NK lysis of K562 target cells, when tested either in medium or in the presence of IL-2, was observed on days 8 and 22 when compared with day 1. Serum samples from selected patients were also evaluated to determine functional IL-2 activity and functional anti-GD2 antibody.

The IL-2 responsive Tf-1b cell line demonstrated IL-2-induced proliferation with patient serum obtained following infusion of hu14.18-IL-2. A progressive increase in proliferation was seen during the first 4 hours following the 4-hour infusion. Values returned to baseline by 16 hours after this infusion, consistent with the serum half-life for hu14.18-IL-2 of approximately 4 hours. Serum samples from these time-points were also examined by flow cytometry for the presence of intact hu14.18-IL-2 immunocytokine (IC) that retains its IL-2 component and its anti-GD2 antibody activity. hu14.18-IL-2 capable of binding to the M21 cell line (GD2 positive) was detectable in patient serum samples following an infusion of IC. The amount of IC able to bind to M21 progressively increased during the first 4 hours following the 4-hour infusion, and decreased after that, again consistent with the half-life of approximately 4 hours.

Finally, in vitro assays were performed with specimens from patients to determine whether administration of hu14.18-IL-2 results in conditions in vivo consistent with those needed to achieve ADCC. PBMCs from day 8 show augmented ADCC on GD2+ target cells when hu14.18-IL-2 is added to the cytotoxic assay. This same ADCC assay was performed with PBMC from day 8, however instead of adding hu14.18-IL-2 to the assay, serum from the patient, obtained before or after hu14.18-IL-2 administration, was added. PBMC obtained from patients on day 8 of course 2 were able to mediate augmented killing of the LA-N-5 cell line in the presence of serum obtained following hu14.18-IL-2 administration, compared to that observed with serum obtained prior to infusion. Thus the hu14.18-IL-2 circulating in patients after IV administration is able to facilitate ADCC with PBMCs activated in vivo by hu14.18-IL-2 from that same patient.

In summary, these results indicate that there were immunological changes associated with this hu14.18-IL-2 therapy including an increase in lymphocyte count, an increase in the percentage of CD16+ and CD56+ PBMC, an increase in NK lysis, and an increase in ADCC. Additional evidence for immune activation included an increase in serum levels of CRP and of sIL-2R. Laboratory analyses of serum and PBMC showed that the hu14.18-IL-2 molecule circulating in patient serum following IV administration retained its ability to activate IL-2 responsive cells through the IL-2 receptor and retained its ability to bind to GD2 positive tumor cells, and deliver IL-2 to their surface, as detected by flow cytometry. NK cells were activated in vivo based on their ability to mediate NK and ADCC function in vitro. Furthermore, the NK cells activated in vivo by the hu14.18-IL-2 administered to these patients were able to mediate ADCC facilitated by the hu14.18-IL-2 circulating in the serum of those same patients. Thus, conditions to achieve immune activation were achieved in all patients in this study.

INCORPORATION BY REFERENCE

The disclosures of each of the patent documents and scientific publications disclosed herein are incorporated by reference into this application in their entireties.

We claim:

1. An antibody variable region comprising the amino acid sequence set forth in SEQ ID NO: 1.

2. An antibody variable region comprising the amino acid sequence set forth in SEQ ID NO: 2.

3. The antibody variable region of claim 2 further comprising the amino acid sequence set forth in SEQ ID NO: 1.

4. The antibody variable region of claim 3, wherein the amino acid sequences are linked by a disulfide bond.

5. The antibody variable region of claim 3, wherein the amino acid sequences are linked by a peptide bond.

* * * * *